United States Patent
Ruhling et al.

(10) Patent No.: US 7,753,914 B2
(45) Date of Patent: Jul. 13, 2010

(54) ORTHOPAEDIC GAGE, KIT AND ASSOCIATED METHOD

(75) Inventors: Marc E. Ruhling, Goshen, IN (US); Anthony J. Metzinger, Winona Lake, IN (US); Berton R. Moed, St. Louis, MO (US); J. Tracy Watson, Town and Country, MO (US)

(73) Assignee: DePuy Products, Inc., Warsaw, IN (US)

( * ) Notice: Subject to any disclaimer, the term of this patent is extended or adjusted under 35 U.S.C. 154(b) by 885 days.

(21) Appl. No.: 11/238,456

(22) Filed: Sep. 29, 2005

(65) Prior Publication Data

US 2007/0088365 A1 Apr. 19, 2007

(51) Int. Cl.
*A61B 17/88* (2006.01)
(52) U.S. Cl. ...................................... 606/102
(58) Field of Classification Search .................. 606/80, 606/96, 102
See application file for complete search history.

(56) References Cited

U.S. PATENT DOCUMENTS

| | | | |
|---|---|---|---|
| 4,612,922 A | 9/1986 | Barber | |
| 4,903,691 A | 2/1990 | Heinl | |
| 4,978,351 A | 12/1990 | Rozas | |
| 5,026,376 A | 6/1991 | Greenberg | |
| 5,133,720 A | 7/1992 | Greenberg | |
| 5,180,388 A * | 1/1993 | DiCarlo | 606/60 |
| 5,409,493 A * | 4/1995 | Greenberg | 606/96 |
| 5,458,602 A | 10/1995 | Goble et al. | |
| 5,746,743 A | 5/1998 | Greenberg | |
| 5,810,828 A | 9/1998 | Lightman et al. | |
| 5,851,207 A | 12/1998 | Cesarone | |
| 5,895,389 A | 4/1999 | Schenk et al. | |
| 5,989,025 A | 11/1999 | Conley | |
| 6,129,729 A | 10/2000 | Snyder | |
| 6,210,415 B1 | 4/2001 | Bester | |
| 6,379,364 B1 | 4/2002 | Brace et al. | |
| 6,635,061 B1 | 10/2003 | Snyder | |
| 6,739,872 B1 | 5/2004 | Turri | |
| 2002/0041797 A1 | 4/2002 | Salice | |
| 2003/0069581 A1 | 4/2003 | Stinson et al. | |
| 2003/0212405 A1 | 11/2003 | Choi | |
| 2004/0049195 A1 | 3/2004 | Singhatat et al. | |
| 2004/0077940 A1 | 4/2004 | Kienzle, III et al. | |
| 2004/0087953 A1 | 5/2004 | Singhatat et al. | |
| 2007/0088364 A1 * | 4/2007 | Ruhling et al. | 606/102 |

FOREIGN PATENT DOCUMENTS

| | | |
|---|---|---|
| EP | 0361641 B1 | 9/1995 |
| EP | 0796593 A2 | 9/1997 |
| EP | 0796593 A3 | 9/1997 |
| EP | 0696904 B1 | 12/1999 |

(Continued)

*Primary Examiner*—Eduardo C Robert
*Assistant Examiner*—Elana B Fisher

(57) ABSTRACT

A depth gage for use with a drill in orthopaedics is provided. The depth gage includes a body. The body has first and second ends opposed to each other and an inner periphery defining a longitudinal aperture through the body for slidably receiving the drill. The longitudinal aperture defines a longitudinal axis of the longitudinal aperture. The body is adapted to permit the drill to be positioned in the longitudinal aperture in a direction non-coincident with the longitudinal axis.

7 Claims, 27 Drawing Sheets

FOREIGN PATENT DOCUMENTS

| | | |
|---|---|---|
| EP | 1374784 A1 | 1/2004 |
| WO | WO 92/00773 A1 | 1/1992 |
| WO | WO 97/43981 A1 | 11/1997 |
| WO | WO 98/53942 A1 | 12/1998 |
| WO | WO 00/27296 A1 | 5/2000 |

* cited by examiner

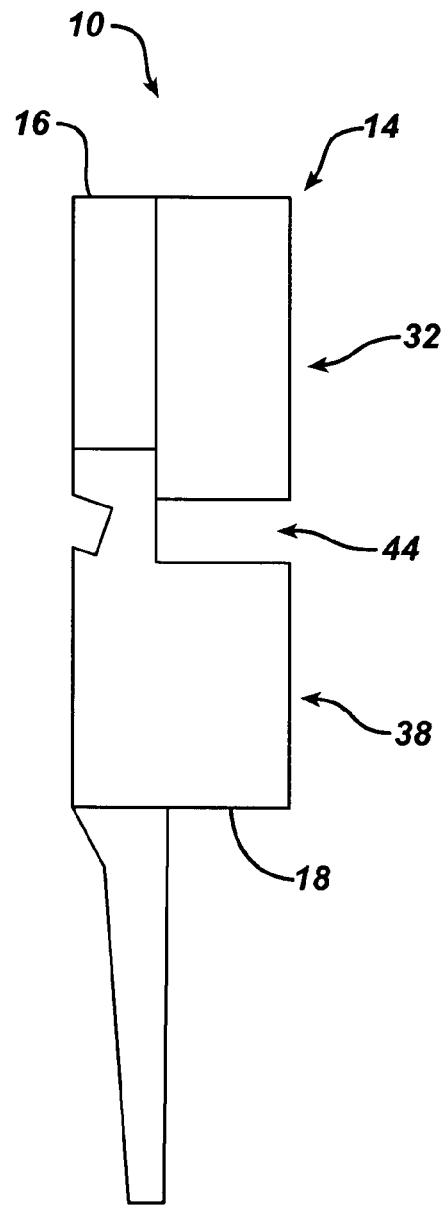
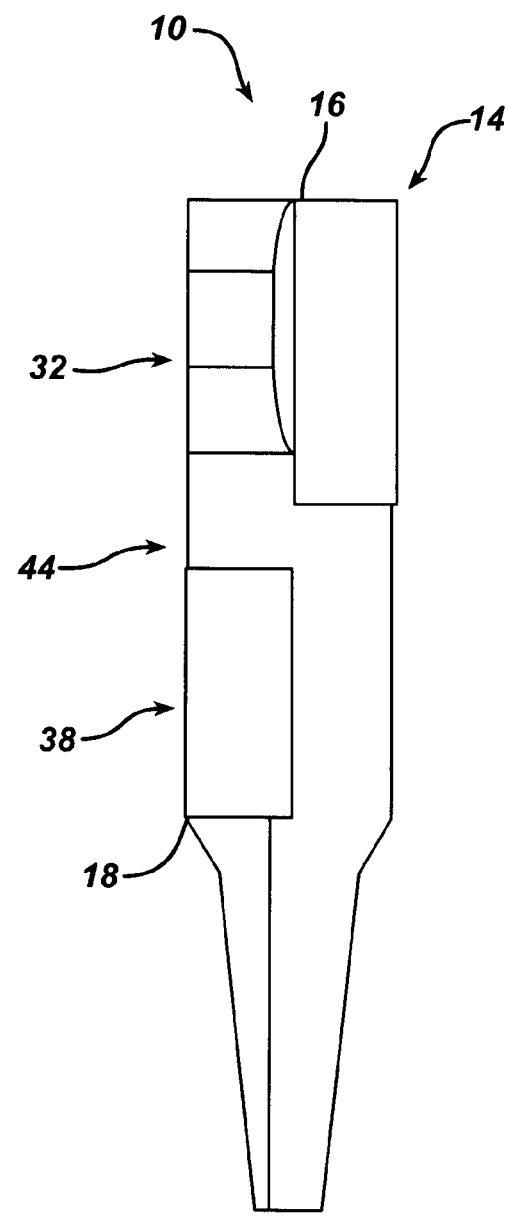
FIG. 6     FIG. 7

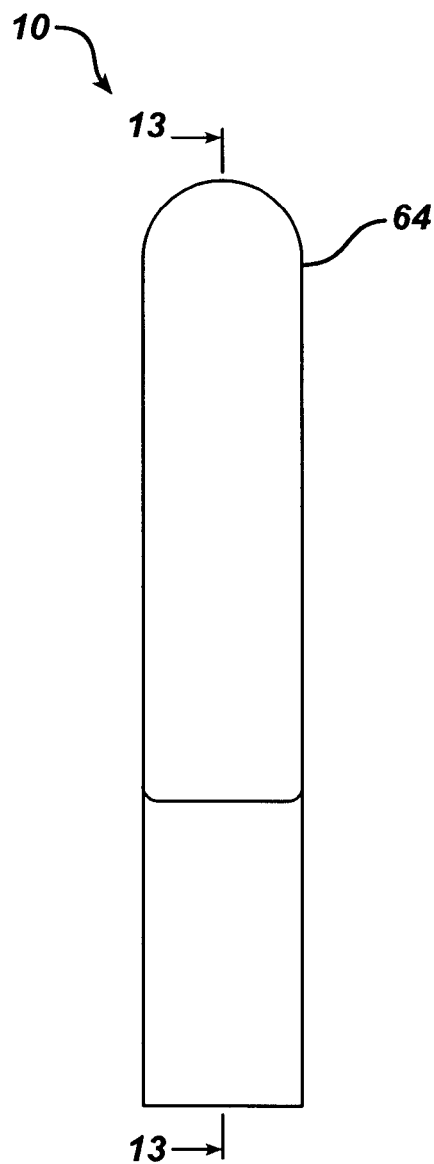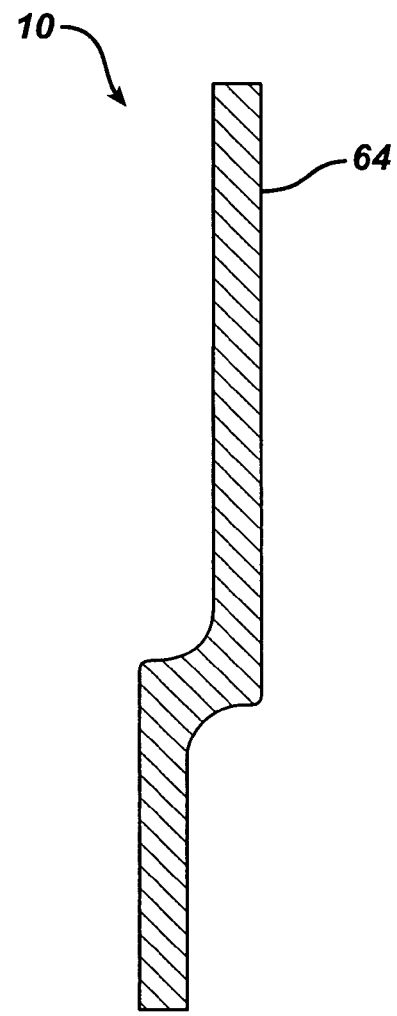
FIG. 12  FIG. 13

ORTHOPAEDIC GAGE, KIT AND ASSOCIATED METHOD

CROSS-REFERENCE TO RELATED APPLICATIONS

Cross-reference is made to the following application: U.S. patent application Ser. No. 11/238,455 titled "TRAUMA GAGE, KIT AND ASSOCIATED METHOD" filed concurrently herewith which is incorporated herein by reference.

TECHNICAL FIELD OF THE INVENTION

The present invention relates generally to the field of orthopaedics, and more particularly, to a device for securing a prosthetic component to bone for use in orthopaedic trauma or orthopaedic joint products.

BACKGROUND OF THE INVENTION

The skeletal system includes many long bones that extend from the human torso. These long bones include the femur, fibula, tibia, humerus, radius and ulna. These long bones are particularly exposed to trauma from accidents, and as such -often are fractured during such trauma and may be subject to complex devastating fractures.

Automobile accidents, for instance, are a common cause of trauma to long bones. In particular, the femur and tibia frequently fracture when the area around the knee is subjected to a frontal automobile accident.

Often the distal end or proximal portions of the long bone, for example the femur and the tibia, are fractured into several segments and must be realigned. Mechanical devices, commonly in the forms of pins, plates, screws, nails, wires and external devices are commonly used to attach fractured long bones. The pins, plates, wires, nails and screws are typically made of a durable material compatible to the human body, for example titanium, stainless steel or cobalt chromium alloys.

Fractures of the long bone are typically secured into position by at least one of three possible techniques.

The first method is the use of intramedullary nails that are positioned in the intramedullary canal of those portions of the fractured bone.

A second method of repairing fractured bones is the use of internal bone plates that are positioned under the soft tissue and on the exterior of the bone and bridge the fractured portion of the bone.

Another method of securing fractured bones in position is the use of external fixators. These external fixators have at least two general categories. In one category the fixator is generally linear with a first portion of the fixator to connect to a first fracture segment of the bone and a second fracture segment of the fixator to connect to the second fracture segment of the bone. A first series of bone screws or pins are first connected to the fixator and then into the first portion of the bone. Then a second series of screws or pins are connected to the fixator and then to the second fracture segment of the bone, thereby securing the first portion fracture segment of the bone to the second portion of the bone.

A second method of external fixation is through the use of a ring type fixator that uses a series of spaced-apart rings to secure the bone. For example, an upper ring and a lower ring are spaced apart by rods. A plurality of wires is placed through the long bone and is connected on each end of the long bone by the ring. The wires are then tensioned much as spokes in a bicycle are tightened, thereby providing for a rigid structure to support the first fracture segment portion of the bone. Similarly, a plurality of wires are positioned through the second fracture segment of the bone and are secured to and tensioned by the lower ring to provide a rigid fixation of the second fracture segment of the bone bridging the fracture site.

There are a variety of devices used to treat femoral fractures. Fractures of the neck, head or intertrochanter of the femur have been successfully treated with a variety of compression screw assemblies, which include generally a compression plate having a barrel member, a lag screw and a compressing screw. The compression plate is secured to the exterior of the femur and the barrel member is inserted into a predrilled hole in the direction of the femoral head.

The lag screw, which has a threaded end and a smooth portion, is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted. The smooth portion of the lag screw must be free to slide through the barrel member to permit the adjustment of the compression screw.

Subtrochanteric and femoral shaft fractures have been treated with the help of intramedullary rods, which are inserted into the marrow canal of the femur to immobilize the femur parts involved in fractures. One or more single angled cross-nail or locking screw may be inserted through the femur and the proximal end of the intramedullary rod. In some varieties, one or two screws may also be inserted through the femoral shaft and through the distal end of the intramedullary rod. The standard intramedullary rods have been successfully employed in treating fractures in lower portions of the femoral shaft.

Similarly, the tibia shaft fractures are frequently treated with the help of intramedullary rods. The intramedullary rods are inserted into the marrow canal of the tibia to immobilize the tibia parts involved in the fractures. Transverse screws may be inserted in apertures formed in the intramedullary rod. The transverse screws are secured to the cortical bone of the tibia.

In both femoral shaft fractures and tibial shaft fractures when intramedullary rods are used the proper transverse screw must be selected for use in the transverse openings of the intramedullary rod after the bone shaft has been drilled to prepare the bone for receiving the transverse screw. It should be appreciated that with other intramedullary rods, such as those for the humerus or any other long bone in the body, the same concern about selecting the proper transverse screw for the intramedullary rod assembly is needed.

The proper length of the transverse screw for use with the intramedullary rod preferably has sufficient length to receive both cortices of the bone shaft. Also, it should be appreciated that the screw is preferably no longer than necessary to engage both cortical walls so that the minimal soft tissue damage occurs.

Several prior art attempts have been utilized to measure the distance between the medial and lateral cortical surfaces of a long bone, for example, a tibia. For example, Smith & Nephew, Memphis, Tenn., has a separate drill guide and measuring instrument. Screw length measurements are accomplished by laying a callipered instrument over the leg and taking an x-ray image of the anterior-posterior view. The measurement is read from the image. The requirement of an x-ray image adds significant time to the procedure and exposes the patient to more radiation than is otherwise necessary.

Stryker Corporation, Kalamazoo, Mich., provides a screw length-measuring device in which the length of the distal screw is measured by drilling the bone, then sliding a gage, which is semi-circle in cross-section on the drill bit. The surgeon is required to hold the measuring device against the drill bit while he takes the reading.

Synthes, Switzerland, provides a procedure for measuring the length of the transverse screw which includes the steps of drilling the bone, removing the drill and drill bit, and inserting a depth gage into the drilled hole for measurement of the required screw length. This procedure adds significant time to the procedure.

The present invention is directed at solving at least some of the afore-mentioned problems.

SUMMARY OF THE INVENTION

The present invention relates to instruments used during the insertion of an intramedullary nail into the canal of a bone for the treatment of fractures in the long bone. Intramedullary nails are normally locked distally with oblique and transverse bone screws. The present instrument and associated calibrated drill are used to take a direct measurement of the appropriate screw length needed for the distal holes of the intramedullary nails. The length measured by the instrument is the distance between the medial and lateral cortical surfaces of the long bone.

The intramedullary nail sleeve and calibrated drill of the present invention provides means for drilling a pilot hole for a bone screw in the long bone. The sleeve is used in-junction with the drill to measure the appropriate length of the necessary bone screw directly off the calibration indicia on the drill bit. The drill sleeve and calibrated drill will allow the user to snap the drill sleeve onto the drill and directly read the drill penetration depth into the bone with both ends of the drill constrained and in location. The ability to read with the drill and drill sleeve in position eliminates the need to complete the drilling process and remove the drill prior to measuring the drill depth. The drilling sleeve need not be pre-assembled to the drill. The device also eliminates the need to remove the drill and insert a secondary gage instrument for a screw length measurement. This eliminates the need to remove the drill and thus shortens the time it takes to drill and measure the drill penetration depth in the bore.

The drill sleeve is positioned so that the drill fits in the space between the portions of the drill sleeve. The drill sleeve snaps into place on the drill bit. The snapping in is accomplished by rotating the drill sleeve in a counter clockwise motion from its original position. The snap on feature actually holds the sleeve on the drill bit once released. The method of reading the calibrations on the drill bit includes the steps of taking the drill penetrations and corresponding screw length measurements with the device. The use of the device eliminates the need for imaging reducing the radiation experienced by the patient. The method and instruments of the present invention allows the surgeon to free the surgeon's hands with the device in place and eliminates the needs to remove the drill and measure with a secondary device.

According to one embodiment of the present invention, there is provided a depth gage for use with a drill in orthopaedics. The depth gage includes a body. The body has first and second ends opposed to each other and an inner periphery defining a longitudinal aperture through the body for slidably receiving the drill. The longitudinal aperture defines a longitudinal axis of the longitudinal aperture. The body is adapted to permit the drill to be installed into the longitudinal aperture in a direction non-coincident with the longitudinal axis.

According to another embodiment of the present invention there is provided a depth gage for use with a drill in trauma surgery. The gage cooperates with the drill for measuring the depth of the drill in a long bone when implanting an intramedullary nail in a patient. The depth gage including a body. The body defines first and second ends opposed to each other and an inner periphery defining a longitudinal aperture through the body for slidably receiving the drill. The longitudinal aperture defines a longitudinal axis of the longitudinal aperture. The body is adapted to permit the drill to be installed into the longitudinal aperture in a direction non-coincident with the longitudinal axis.

According to yet another embodiment of the present invention there is provided a kit for use in orthopaedics. The kit includes a drill including a depth indicating feature. The kit also includes a the depth gage having a body. The body defines first and second ends opposed to each other and an inner periphery defining a longitudinal aperture through the depth gage for slidably receiving the drill. The longitudinal aperture defines a longitudinal axis of the longitudinal aperture. The body is adapted to permit the drill to be installed into the longitudinal aperture in a direction non-coincident with the longitudinal axis. The body includes a drill cooperating feature for cooperating with the depth indicating feature of the drill.

According to another embodiment of the present invention there is provided a kit for use in orthopaedics. The kit includes an intramedullary nail, a screw, and a drill including a depth indicating feature. The kit also includes a depth gage including a body. The body defines first and second ends opposed to each other and an inner periphery defining a longitudinal aperture through the body for slidably receiving the drill. The longitudinal aperture defines a longitudinal axis of the longitudinal aperture. The body is adapted to permit the drill to be positioned in the longitudinal aperture in a direction non-coincident with the longitudinal axis. The body includes a drill cooperating feature for cooperating with the depth indicating feature of the drill.

According to a further embodiment of the present invention, there is provided a method for performing orthopaedic surgery on a long bone. The method includes the steps of providing a drill including a depth indicating feature and drilling a hole in the long bone with the drill. The method also includes the step of providing a depth gage including a body. The body defines first and second ends opposed to each other and an inner periphery defining a longitudinal aperture through the body for slidably receiving the drill. The body includes a drill cooperating feature. The method further includes the step of positioning the drill in the longitudinal aperture of the body of the depth gage in a direction non-coincident with the longitudinal axis of the body of the depth gage. The method further includes the step of using the drill cooperating feature of the body of the depth gage and the depth indicating feature of the drill to determine the depth of the drill in the bone.

According to a further embodiment of the present invention, there is provided a method for implanting an intramedullary nail in a long bone. The method includes the steps of providing an intramedullary nail, preparing the long bone for the intramedullary nail, and implanting the intramedullary nail in the long bone. The method further includes the steps of providing a drill including a depth indicating feature and drilling a hole in the long bone and through the intramedullary nail with the drill. The method further includes the step of providing a depth gage including a body. The body defines first and second ends opposed to each other and an inner periphery defining a longitudinal aperture therethrough for slidably receiving the drill. The body includes a drill cooperating feature. The method further includes the step of positioning the drill in the longitudinal aperture of the body of the depth gage in a direction non-coincident with the longitudinal axis on the body of the depth gage. The method further includes the step of using the drill cooperating feature of the body of the depth gage and the depth indicating feature of the drill to determine the depth of the drill in the bone.

The technical advantages of the present invention include the ability to install the sleeve without removal of the drill from the bone. For example, according to one aspect of the present invention, the sleeve includes features to provide for the ability to radially assemble the sleeve unto the drill. Thus, the present invention provides for the ability to install the sleeve without removing the drill from the bone.

The technical advantages of the present invention further include the ability of the sleeve to remain constrained on the drill. When the sleeve is constrained on the drill the surgeon does not need to hold on to the sleeve. This permits the surgeon to perform other techniques on the patient. For example, according to another aspect of the present invention, the sleeve includes a snapping feature which, as the sleeve is inserted around the drill, the sleeve snaps into position on the drill. Thus, the present invention provides for the ability of the sleeve to remain constrained on the drill.

The technical advantages of the present invention further include the ability to easily snap the sleeve into place. For example, according to yet another aspect of the present invention, the sleeve includes a two way ramp to gently deflect the sleeve so that it may easily snap in place on the drill. Thus, the present invention provides for the ability to easily snap the sleeve into place on the drill.

Other technical advantages of the present invention will be readily apparent to one skilled in the art from the following figures, descriptions and claims.

BRIEF DESCRIPTION OF THE DRAWINGS

FIG. 6 is a plan view of the sleeve of FIG. 5;

FIG. 7 is a top view of the sleeve of FIG. 5;

FIG. 12 is a plan view of the handle of FIG. 10;

FIG. 13 is a cross-sectional view of FIG. 12 along the line 13-13 in the direction of the arrows;

Corresponding reference characters indicate corresponding parts throughout the several views. Like reference characters tend to indicate like parts throughout the several views.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
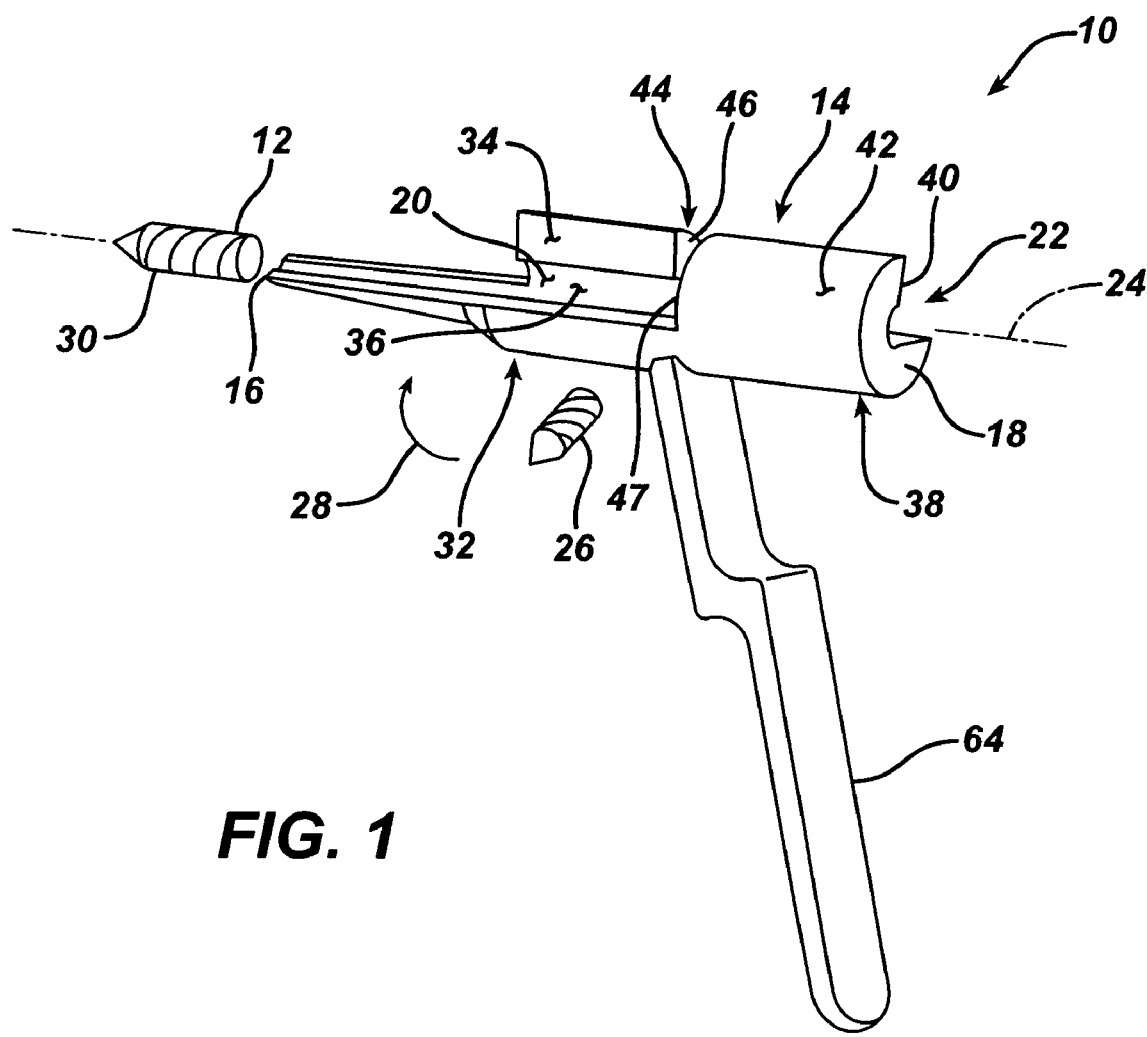
FIG. 1 is a perspective view of a sleeve assembly in accordance to an embodiment of the present invention.

According to the present invention and referring now to FIG. 1, a depth gage 10 for use with a drill 12 in orthopedics is shown. The depth gage 10 includes a body 14. The body 14 defines a first end 16 as well as a second end 18 opposed to the first end 16. The body 14 further defines an inner periphery 20 defining a longitudinal aperture 22 through the body 14. The longitudinal aperture is adapted for slidably receiving the drill 12. The longitudinal aperture 22 defines a longitudinal axis 24 of the longitudinal aperture 22. The body 14 is adapted to receive the drill 12 to be installed in the longitudinal aperture 22 in a direction non-coincident with the longitudinal axis 24. The body 14 is further adapted to restrain the drill 12 within the inner periphery 20 of the body 14.

For example and is as shown in FIG. 1, the depth gage 10 may be adapted to receive the drill 12 to be positioned in the longitudinal opening 22 in a direction normal or perpendicular to the longitudinal axis 24 of longitudinal opening 22. For example and is shown in phantom, the drill 12 may be positioned in first position 26 as shown in phantom.

As shown in FIG. 1, the drill 12 may be placed in first position 26 as shown in FIG. 1 and then rotated in the direction of arrow 28 into second position 30 within the longitudinal aperture 22. The normal insertion of the drill 12 into the depth gage may be accomplished in any suitable way.

For example and is shown in FIG. 1, the depth gage. 10 may include a first hand portion 32 positioned adjacent the first end 16 of the body 14. The first end portion 32 has at least a portion of the first end portion which has a cross-section along a plane 34 perpendicular to the longitudinal axis 24 of the longitudinal aperture 22. The cross-sectional-plane 34 defines an arcuate periphery 36 for close conformance to the drill 12.

The depth gage 10 may further include a second end portion 38 positioned opposed to the first end portion 32 and adjacent end 18 of the body 14. The second end portion 38 has at least a portion thereof, having a cross-section along a plane 40 perpendicular to the longitudinal axis 24 of the longitudinal aperture 22. The plane 40 defines an arcuate periphery 42 for close conformance to the drill 12.

The depth gage 10 may further include a middle portion 44 of the body 14. The middle portion 44 has a portion of the cross-section of the middle portion 44 along plane 46 defining a periphery 47 for intimate contact with the drill 12.

Figure 2:
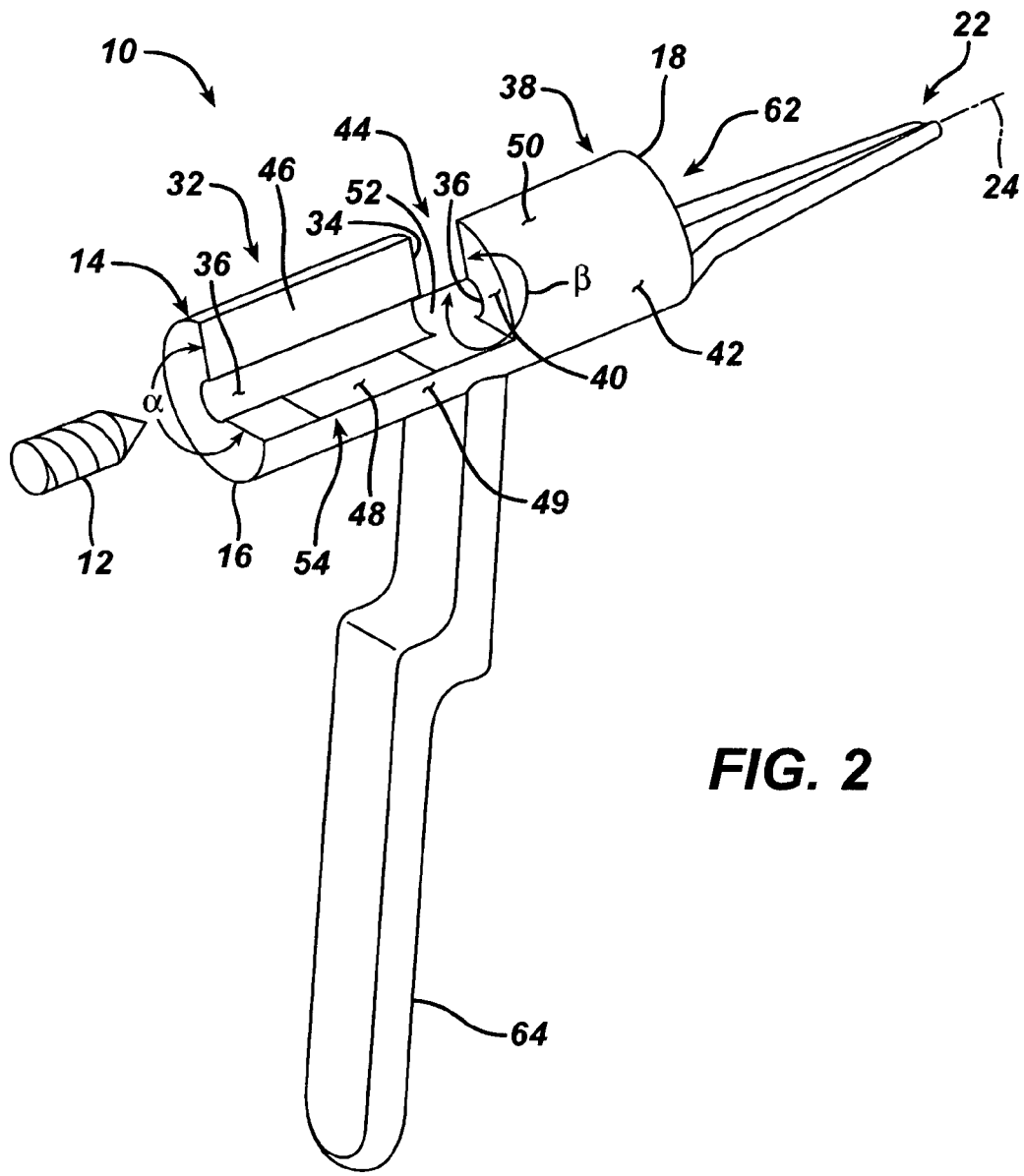
FIG. 2 is another perspective view of the sleeve assembly of FIG. 1.

Referring now to FIG. 2, the depth gage 10 can be configured to restrain the drill 12 within the longitudinal aperture 22 in any suitable manner. For example and shown in FIG. 2, the arcuate periphery 36 of the first end portion 32 may extend at an angle α which is greater than the 180 about longitudinal axis 24 of the longitudinal aperture 22. For example and is shown in FIG. 2, the angle α may be about 270°.

Alternatively or in addition, the arcuate periphery 36 of the second end portion 38 may extend from an angle β which is greater than 180° about longitudinal axis 24 of the longitudinal aperture 22. For example and is shown in FIG. 2, the angle β may be around 270°.

It should be appreciated that the angles α and β may be any angle which is slightly larger than the 180°. For example, the angles α and β may be from 85° to 270° or greater. It should be appreciated that the angle α and β preferably are substantially less than 360° so that the drill 12 may be positioned into the longitudinal aperture 22 of the depth gage 10. For example and is shown in FIG. 2, the first end portion 32 may include a first face 48 extending radially from the longitudinal axis 24 of the longitudinal aperture 22. The first end portion 32 further includes a second face 49 extending radially along the longitudinal axis 24 of the longitudinal aperture 22.

Similarly, the second end portion 38 includes a first face 50 extending radially from the longitudinal axis 24 of the longitudinal aperture 22 as well as a second face 52 extending radially from the longitudinal axis 24 of the longitudinal aperture 22.

As shown in FIG. 2, the first face 46 of the first end portion and the first face 50 of the second end portion 38 are generally coplanar with each other and extend in directions opposed to each other. Similarly, the second face 49 of the first end portion 32 and the second face 52 of the second end portion 38 are generally coplanar and extend in the same direction.

As shown in FIG. 2, the first face 48 of the first end portion 32 may extend generally perpendicularly with respect to the second face 49 of the first end portion 32.

Similarly, the first face 50 of the second end portion 38 may extend generally perpendicularly with respect to the second face 52 of the second end portion 38.

According to the present invention and referring now to FIGS. 1 and 2, the depth gage 10 may include, as is shown in FIGS. 1 and 2, a snap-in feature. The snap-in feature may be associated with either the first end portion 32 or the second end portion 38 or may be associated with both end first portion 32 and the second end portion 38. For example and as is shown in FIGS. 1 and 2, the depth gage 10 may include a first snap-in feature 54 associated with the first end portion 32. The first snap end feature 54 includes the second face 49 as well as an engaging ramp 56 and a disengaging ramp 58.

The drill 12 is loaded against loading face 60 and the drill i-s rotated and moved along engaging ramp 56 toward second face 49. The drill 12 then is moved along disengaging ramp 58 until the drill 12 is positioned in longitudinal aperture 22 of depth gage 10. The engaging ramp 56 is positioned against loading face 60 formed on the middle portion 44 of the depth gage to the second face 49 of the first end portion 22. The first snap-in feature 54 further includes the disengaging ramp 58, which extends from the second face 48 to the first end 16 of the first end portion 32.

Figure 2A:
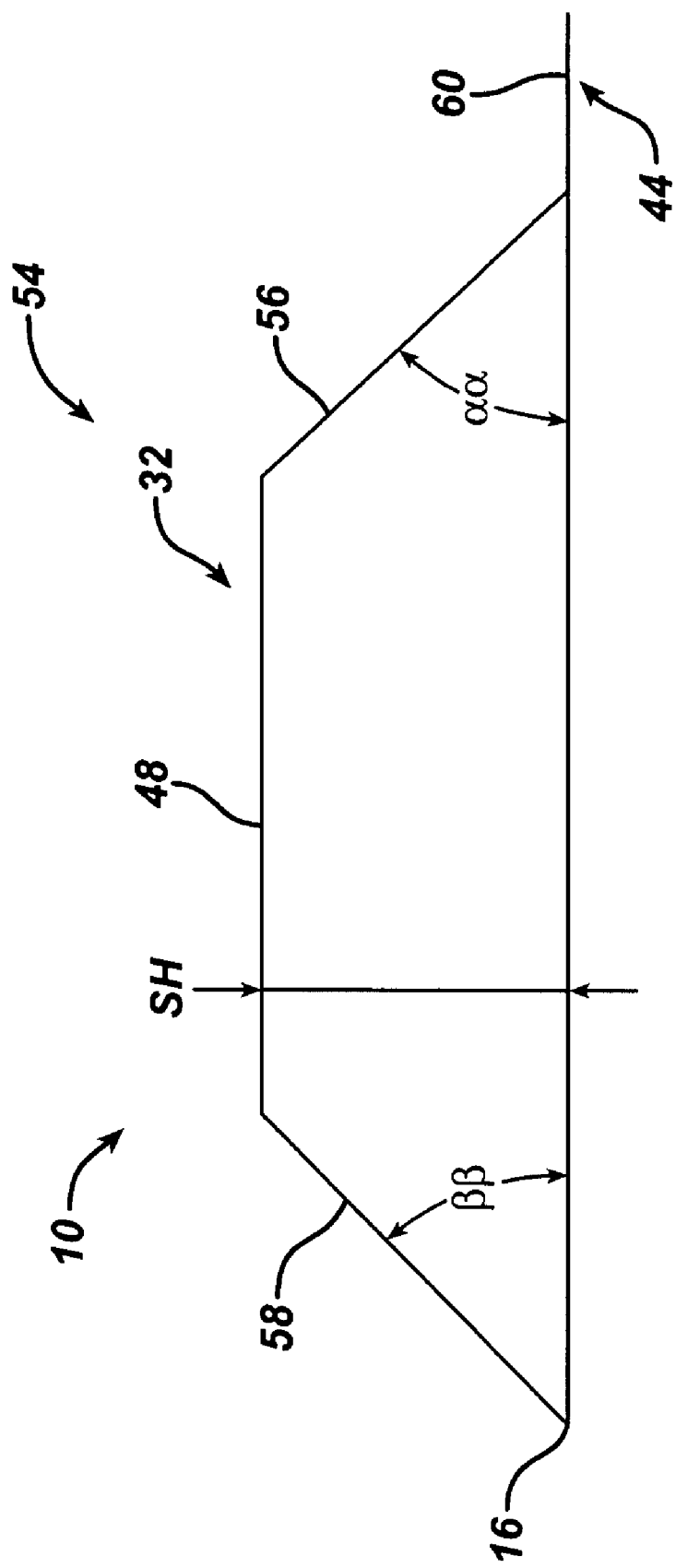
FIG. 2A is a partial plan view of the sleeve assembly of FIG. 2 showing the snap-in ramp in greater detail.

The engaging ramp 56 may form any suitable angle or slope with respect to the loading face 60. For example, the loading face 60 and the engaging ramp 56 may form an acute angle αα therebetween. The angle αα may, for example, be 5° to 35°. The disengaging ramp 58 may have any suitable shape, and may as is shown in FIG. 2A form an angle ββ with respect to the loading face 60. The angle ββ may, for example, be from 10° to 40°. The second face 49 of the snap-in feature 54 may be spaced by any suitable amount from the loading face 60. For example, the second face 49 may be spaced from and may be parallel to the middle portion 44 and be spaced apart a distance defined as snap height SH of, for example, 2 to 6 mm.

While the depth gage of the present invention may include a solitary snap-in feature such as first snap-in feature 54. The depth gage 10 may as is shown in FIG. 1 include a second snap-in feature 62 similar to the first snap-in feature 54. Second snap-in feature 62 may be similar in shape to the first snap in feature 54.

Figure 3:
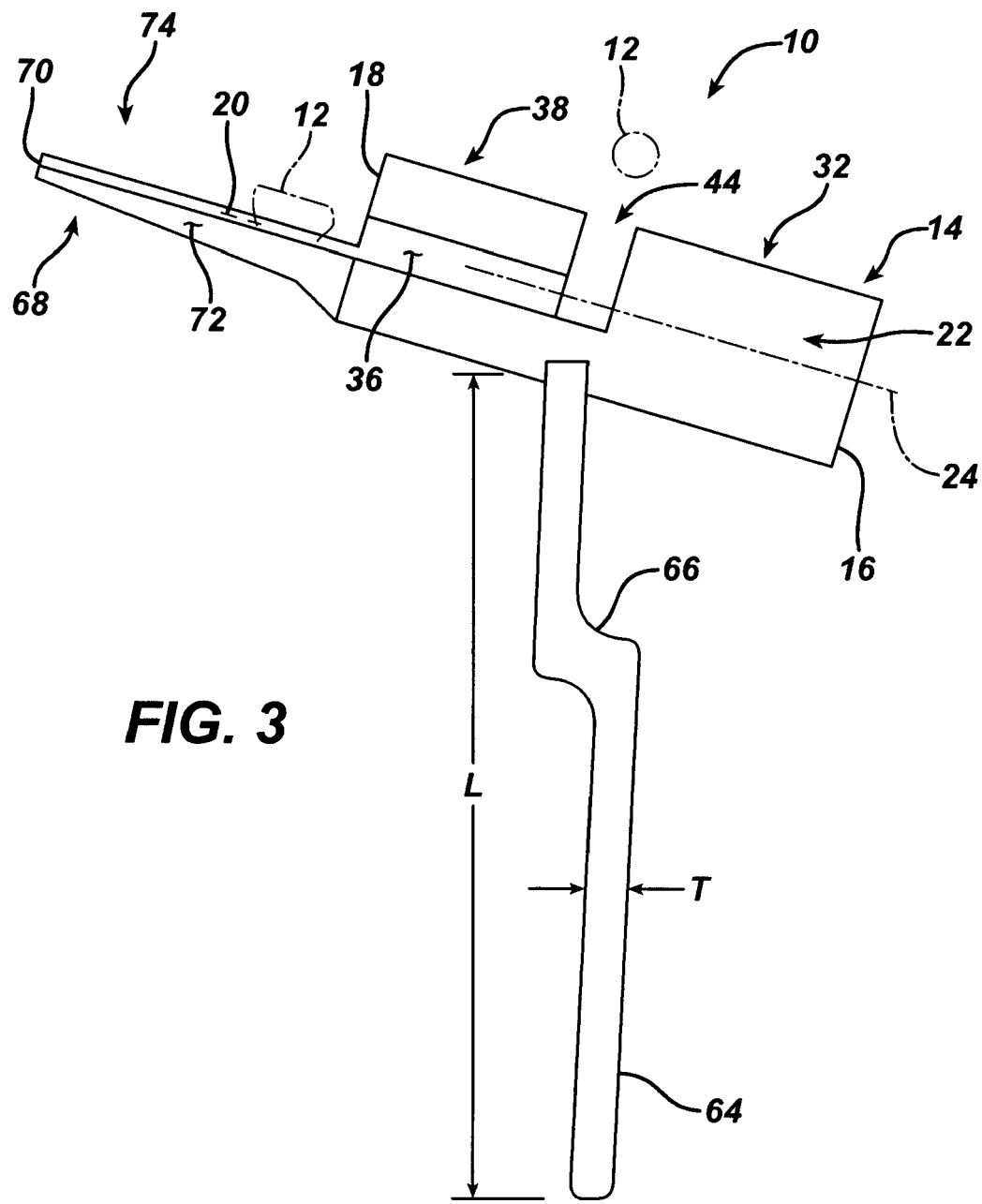
FIG. 3 is a plan view of the sleeve assembly of FIG. 1.
Figure 4:
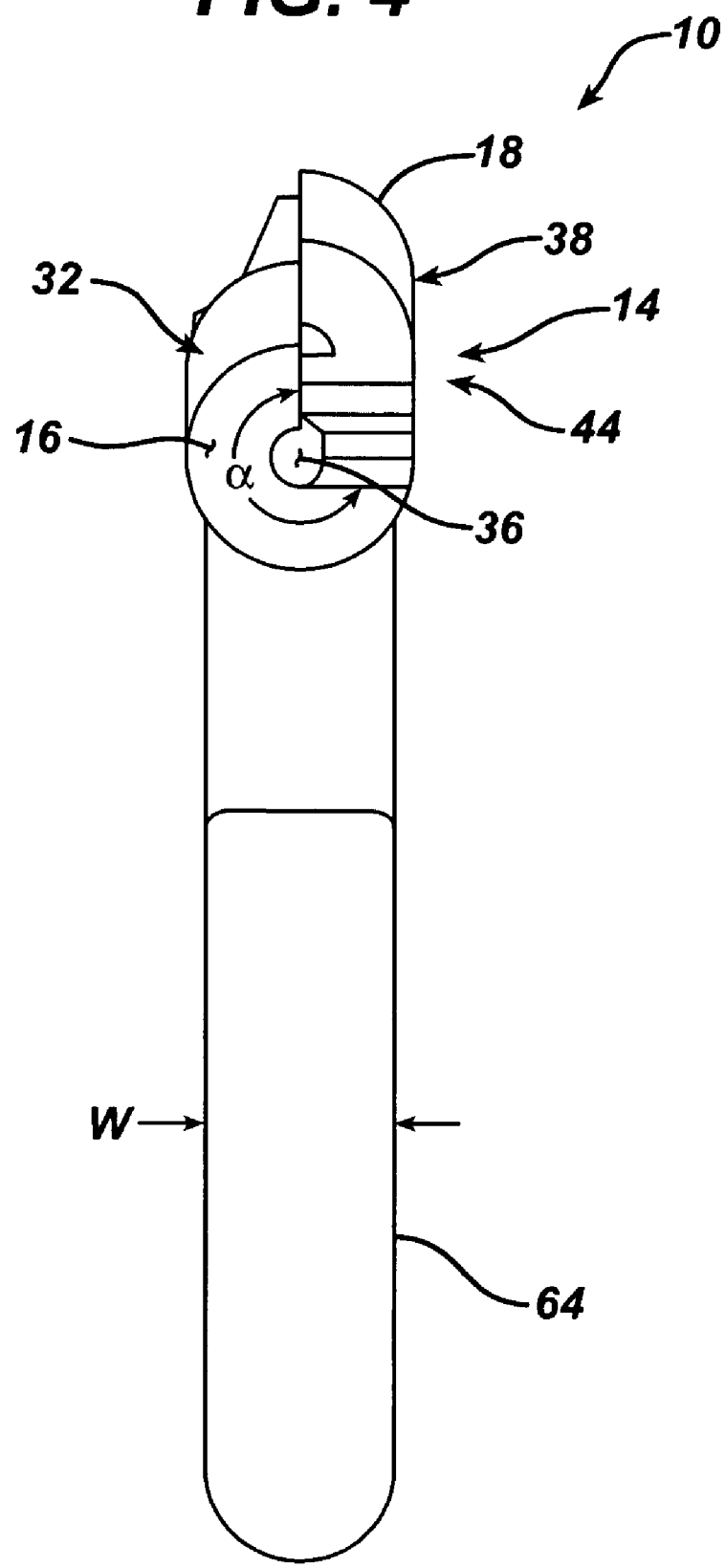
FIG. 4 is a side view of the sleeve assembly of FIG. 1.
Figure 5:
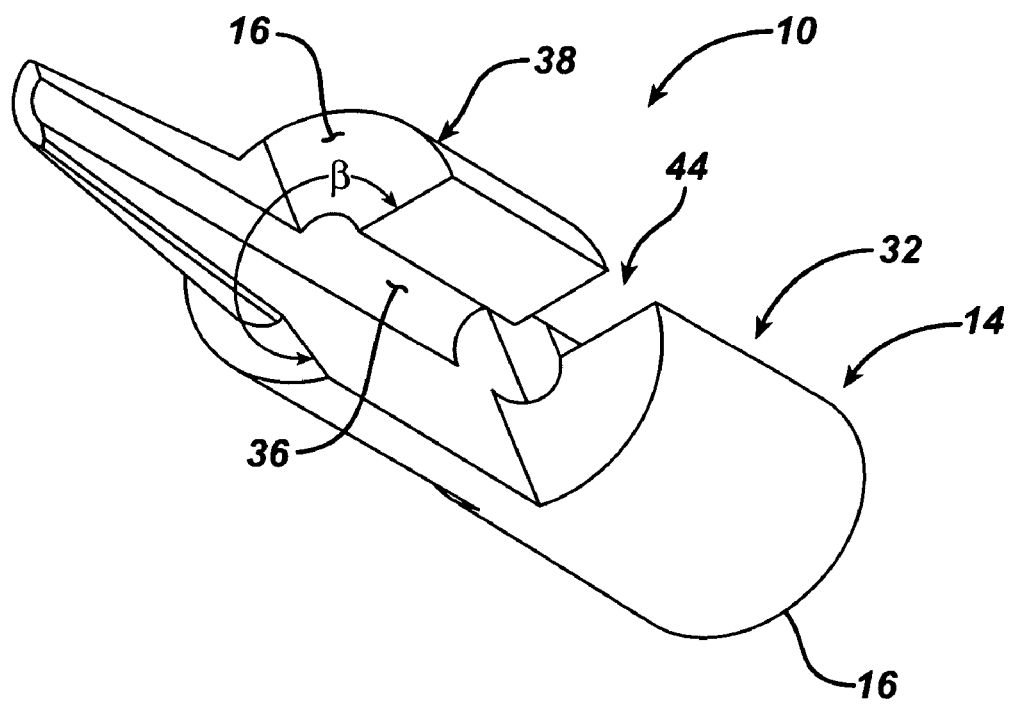
FIG. 5 is a perspective view of the sleeve of the sleeve assembly of FIG. 1.
Figure 8:
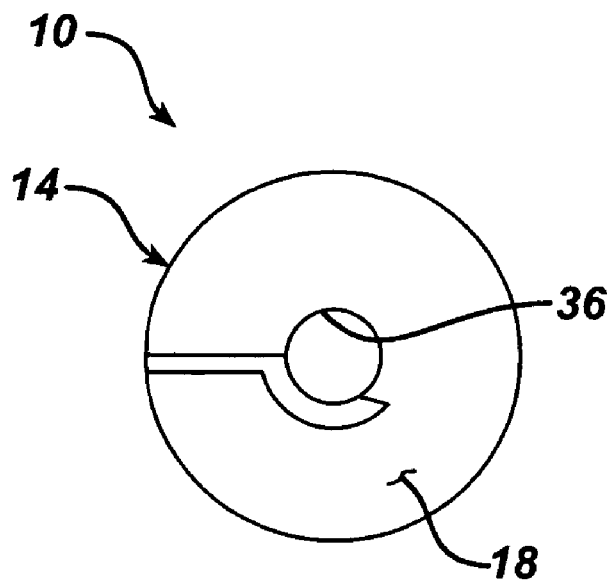
FIG. 8 is a first end view of the sleeve of FIG. 5.
Figure 9:
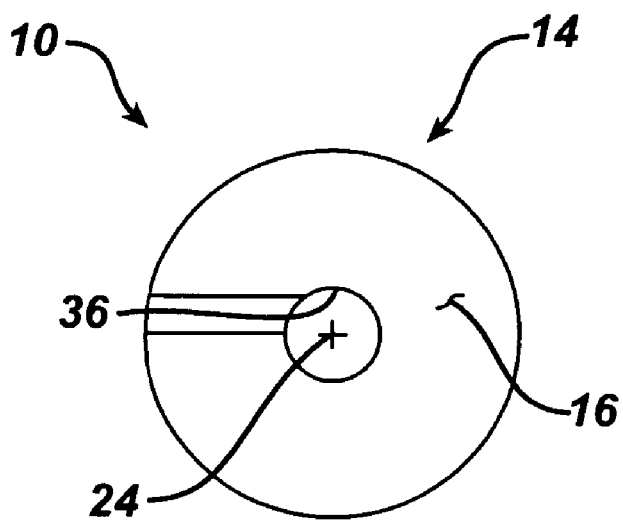
FIG. 9 is a second end view of the sleeve of FIG. 5.
Figure 10:
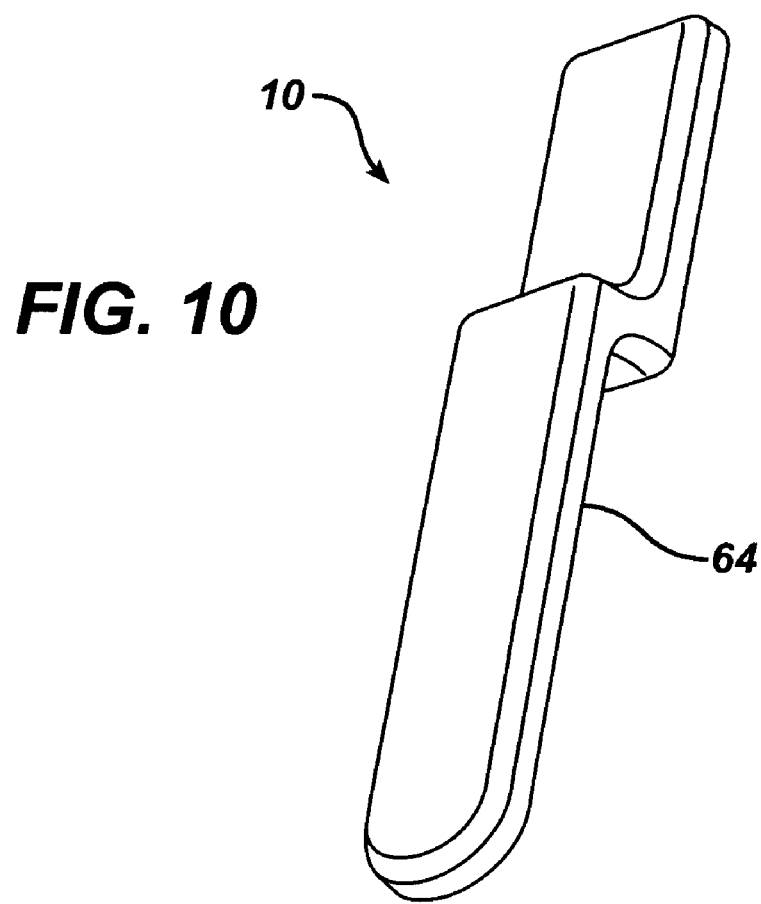
FIG. 10 is a perspective view of the handle of the sleeve assembly of FIG. 1.
Figure 11:
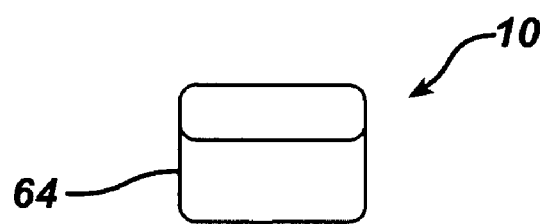
FIG. 11 is an end view of the handle of FIG. 10.

Referring now to FIG. 4, the depth gage 10 may further include a handle 64. The handle 64 may have any suitable shape capable for providing a means for a surgeon to grasp the depth gage 10 to install it on to the drill 12. For example and is shown in FIG. 3, the handle 64 may have an overall length L and a thickness T. The handle 64 may, as is shown in FIGS. 3 and 4, have a generally rectangular shape. The handle 64 may alternatively have a circular oval or any suitable cross section such that has sufficient strength for operating the depth gage 10. The handle 64 as shown in FIG. 3 includes an off set 66 serves to permit the surgeon hand to be in a comfortable position.

Referring now to FIG. 4, the handle 64 further includes a width W. Preferably width W is sufficiently wide to provide sufficient ability for the surgeon to assert enough torque to the depth gage to install the depth gage with the snap-in feature onto the drill 12.

Referring again to FIG. 1-3, the depth gage 10 may include a provision for use in minimally invasive procedures. For example, the depth gage 10 may as shown in FIGS. 1, 2, and 3, include a trocar portion 68 to assist in the insertion of the depth gage 10 through the skin and soft tissue of a patient such that a trocar tip 70 may contact the long bone of the patient. The trocar portion 68 may include an inner periphery for cooperation with the drill 12 and a taper shaped outer periphery 72 for passage of the depth gage 10 through soft tissue of the patient. The trocar portion 68 may include an opening 74 for receiving the drill 12 when it is moved from its first position 26 to its second position 30, as is shown in FIG. 1.

Figures 14, 15:
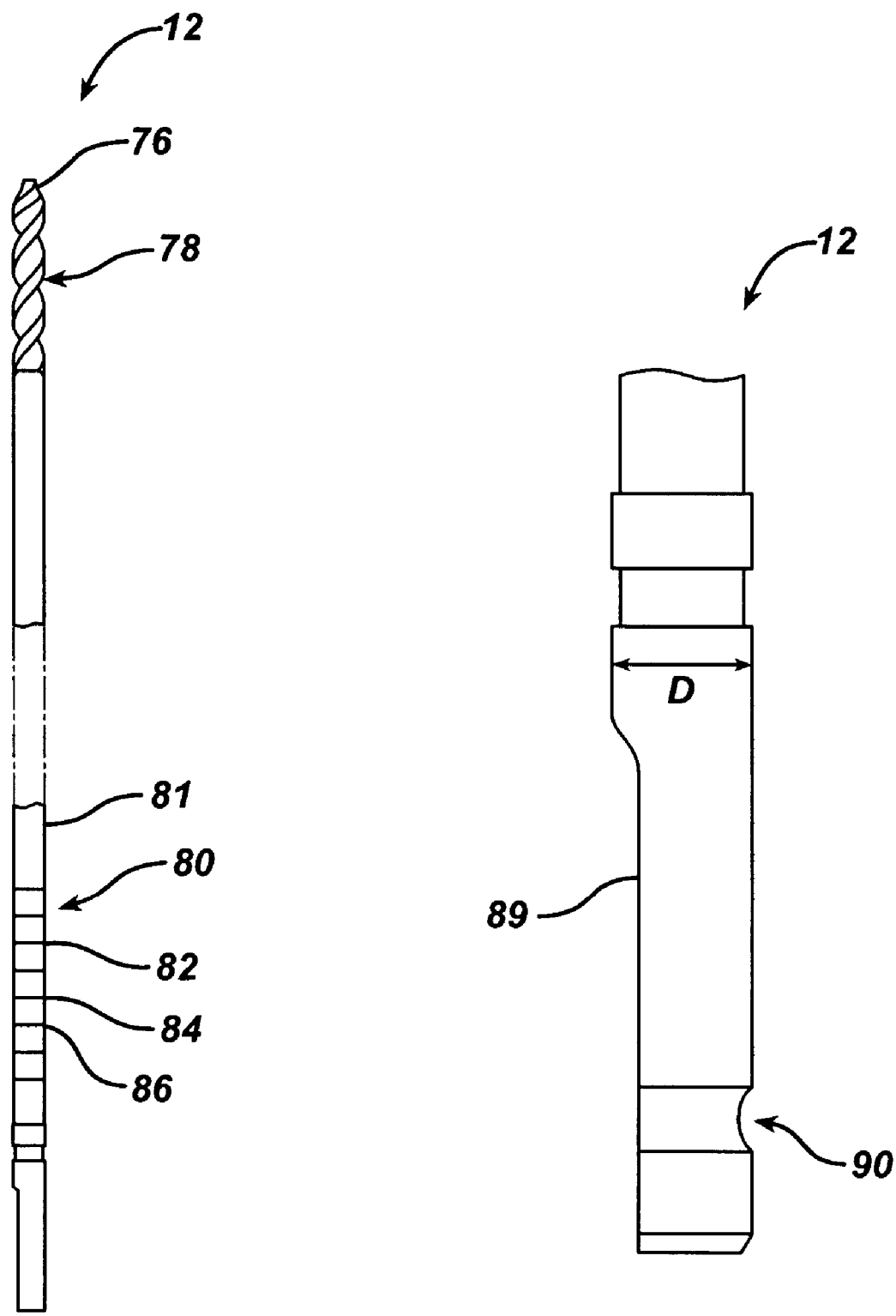
FIG. 14 is a plan view of a drill to be used with the sleeve assembly of FIG. 1.
FIG. 15 is a partial plan view of the shank of the drill of FIG. 14.

Referring now to FIGS. 14 and 15, the drill 12 for use with the depth guide of the present invention is shown in greater detail. The drill 12 includes a cutting edge 76 for removing bone from the long bone. The drill 12 may further include a plurality of, for example, four parallel spaced apart spiral flutes 78 for assisting in removing the bone chips from the drilling site. The bone chips may move spirally up the flutes 78 and out of the bone cavity. Bone chips and bone marrow removed in the drilling process may be worked or irrigated from the surgical site.

The drill 12 is rotated and advanced toward the bone. The drill 12 may be rotated by hand or be rotated by a power tool (not shown). Such power tools are commercially available and may be pneumatic, hydraulic, or preferably electrical, for example, in the form of a battery powered drill. The drill 12, as is shown in FIGS. 14 and 15, includes indicia 80 formed on the shank 81 of the drill 12. The indicia 80 may be in the form of circumferential grooves or marks 82 and may include further indicia in the form of numbers 84 or letters 86. The shank 81 may include a flat 88 and a groove 90 to assist in securing the drill 12 with the power tool (not shown). The shank 81 of the drill may be defined with a circular cross-section having a diameter D for a slidable fit within the periphery 20 of the longitudinal aperture 22 of the depth gage 10.

The indicia 80 are adapted to be positioned adjacent by a portion of depth gage 10 and the indicia 80 represent the relative position of the drill 12 with the respect to the depth gage 10 when the drill has fully cut both cortices of the long bone.

Referring now to FIGS. 16-20, a kit 110 for performing arthoplasty is shown. The kit 110 includes the depth gage 110 and the drill 12. The drill 12 includes a depth indicating feature 80 in the form of, for example, indicia. It should be appreciated that the depth indicating feature 80 may be in the form of a telescopic tube, an arm, or other feature.

The kit 110 also includes the depth gage. The depth gage 10 includes a body 14. The body includes first end 16 and opposed second end 18. The body further defines the inner periphery 20, which defines a longitudinal aperture 22 through the body 14. The longitudinal aperture 22 slidably receives the drill 12. The longitudinal aperture 22 defines a longitudinal axis 24 of the longitudinal aperture 22. The body is adapted to permit the drill 12 to be installed in the longitudinal aperture 22 in a direction non-coincident with the longitudinal axis 24. The body 14 includes a drill cooperating feature in the form of, for example, the first end 16 for cooperating with the depth indicating feature 80 of the drill 12.

Figure 16:
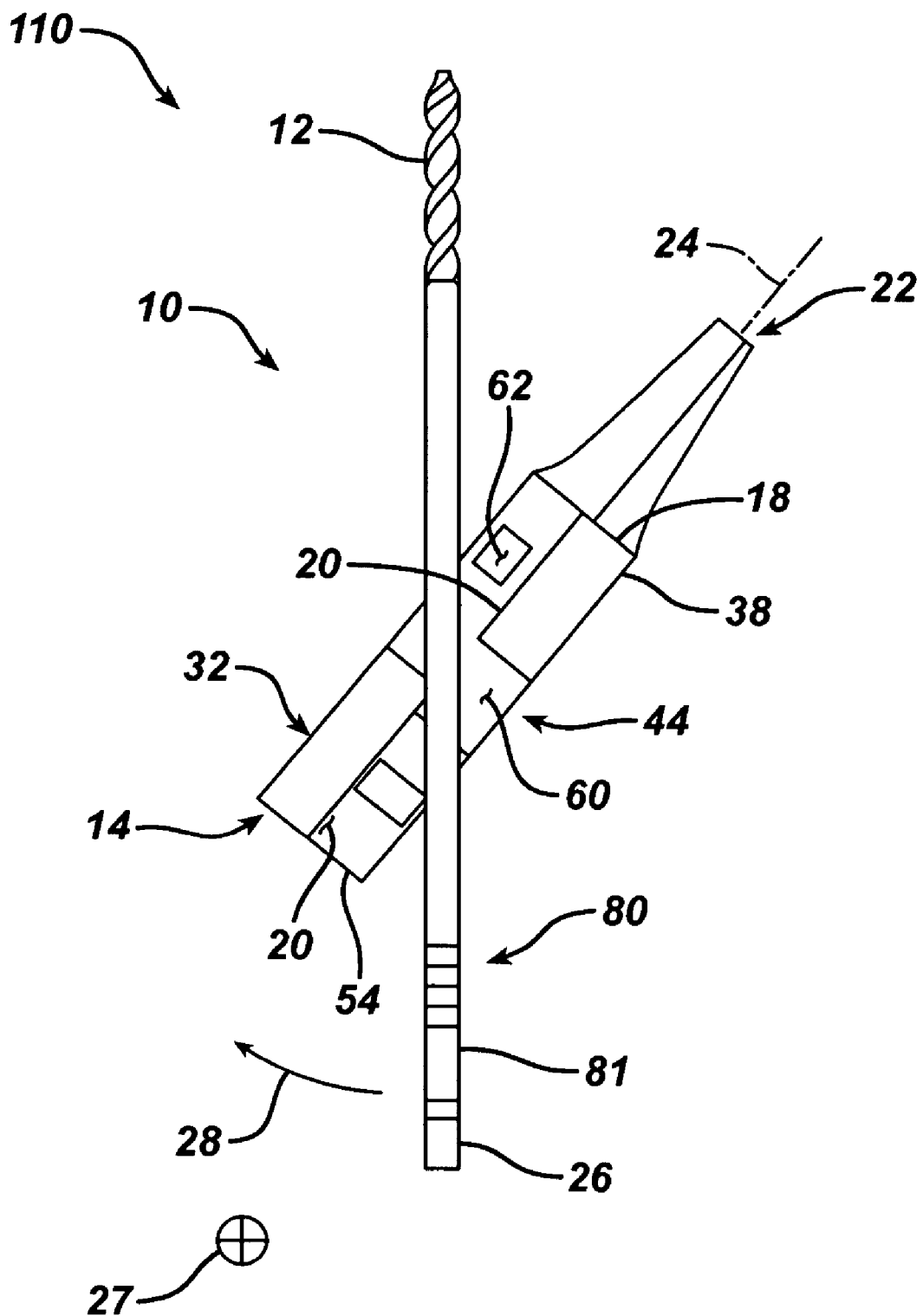
FIG. 16 is a plan view of a kit for performing trauma surgery in accordance to another embodiment of the present invention utilizing the drill of FIG. 14 and the sleeve assembly of FIG. 1 with the drill of FIG. 14 in position to be inserted into the sleeve assembly of FIG. 1.

Referring now to FIG. 16, the drill 12 is shown in first position 26 with respect to the depth gage 10. The drill 12 is installed by advancing the drill in the direction of arrow 28 until the shank 82 of the drill 12 seats against the loading face 60 of the body 14 of the depth gage 12. The drill 12 is passed into the middle portion 44 of the body 12 between first portion 32 and the second portion 38 of the body 14 of the depth gage 10. The drill 12 is then rotated with respect to the drill depth 10 in the direction of arrow 28.

Figure 17:
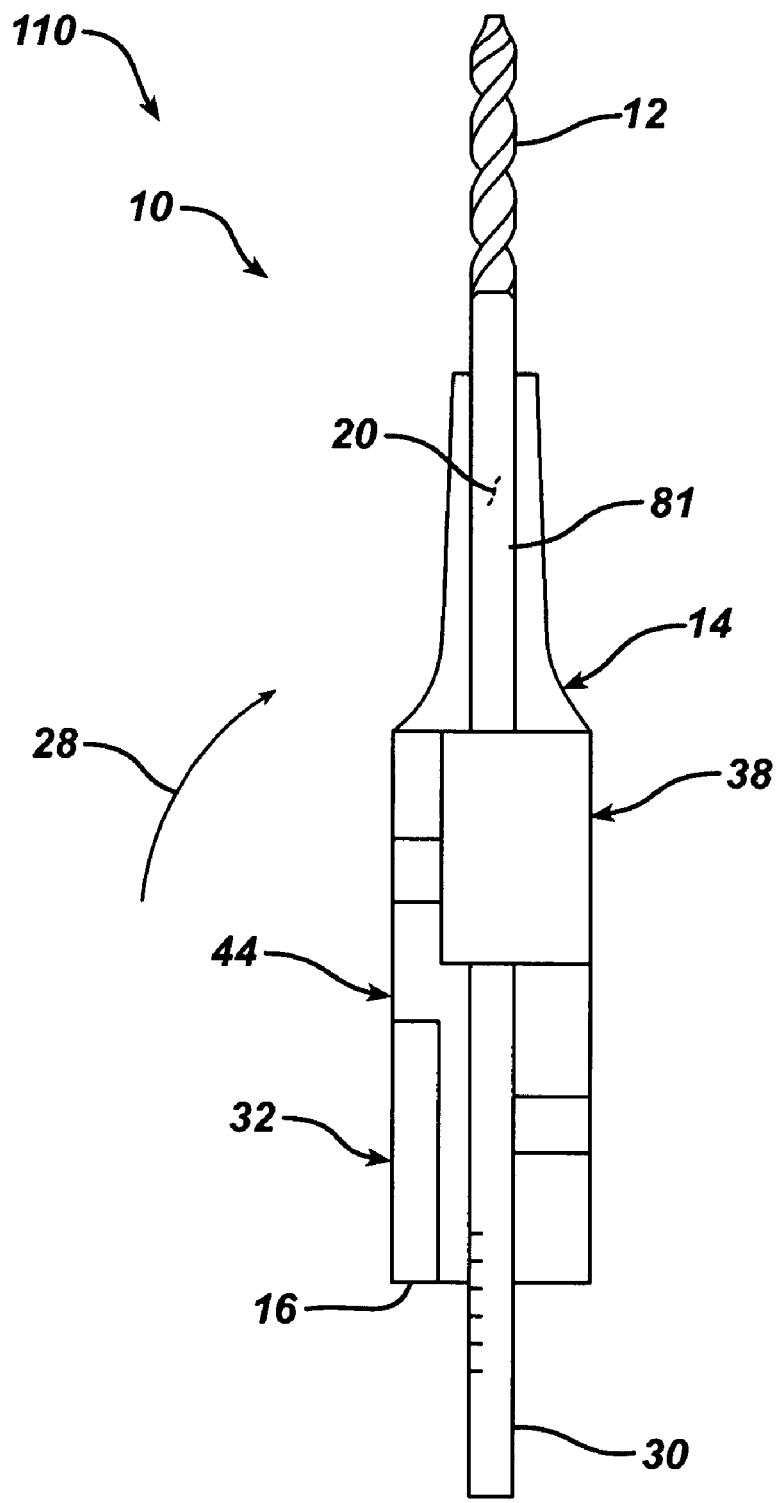
FIG. 17 is a plan view of kit of FIG. 16 with the drill of FIG. 14 in position in the sleeve assembly of FIG. 1.

Referring now to FIG. 17, the drill 12 is shown in second position 30 with respect to the depth gage 10. As shown in FIG. 17, the drill 12 is rotated in the direction of arrow 28 until the shank 82 of the drill 12 seats against inner periphery 20 of the body 14 of the depth gage 10.

Figure 18:
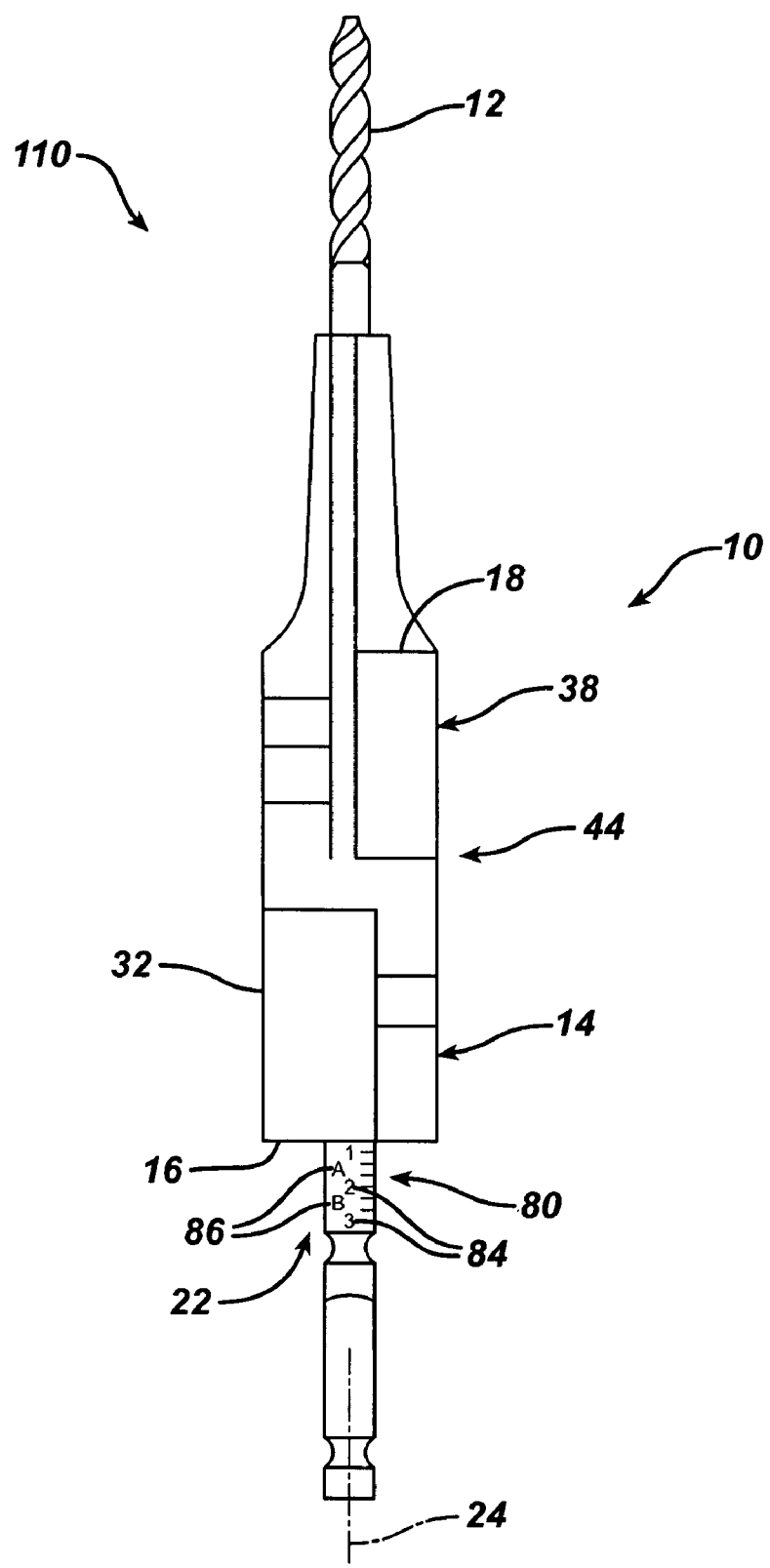
FIG. 18 is another plan view of kit of FIG. 16 with the drill of FIG. 14 in position in the sleeve assembly of FIG. 1.

Referring now to FIG. 18, the indicia 80 of the drill 12 are shown in cooperation with the depth gage 10 to assist in selecting the proper bone screw for the patient.

Figure 20:
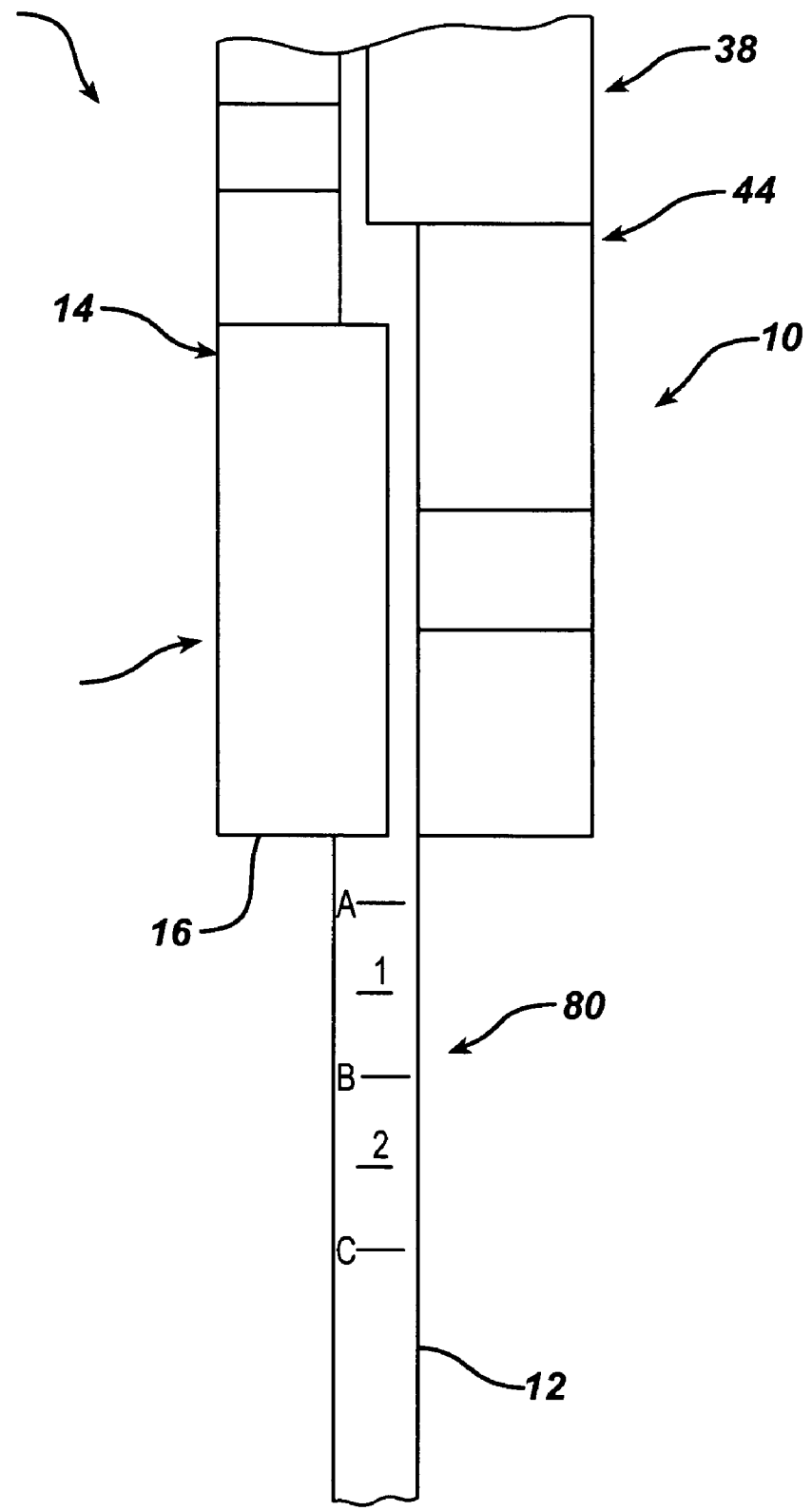
FIG. 20 is an enlarged partial plan view of kit of FIG. 16 with the drill of FIG. 14 in position in the sleeve assembly of FIG. 1.

Referring now to FIG. 20, the indicia 80 are shown in greater detail. For example, and as shown in FIG. 20, the indicia 80 may include marks or transverse circular lines, one of which mates with or aligns with the first end 16 of the body 14 of the depth gage 10.

Referring now to FIG. 18, for each mark 82, a number 84, or a letter 86 may correspond to it. For example and is shown in FIG. 18, the first end 16 is in alignment with mark 82 having a number 6. For example, the number 6 may represent a cortical bone screw having a determined length. The screw 6 should be used when the depth gage registers as shown in FIG. 18.

Figure 19:
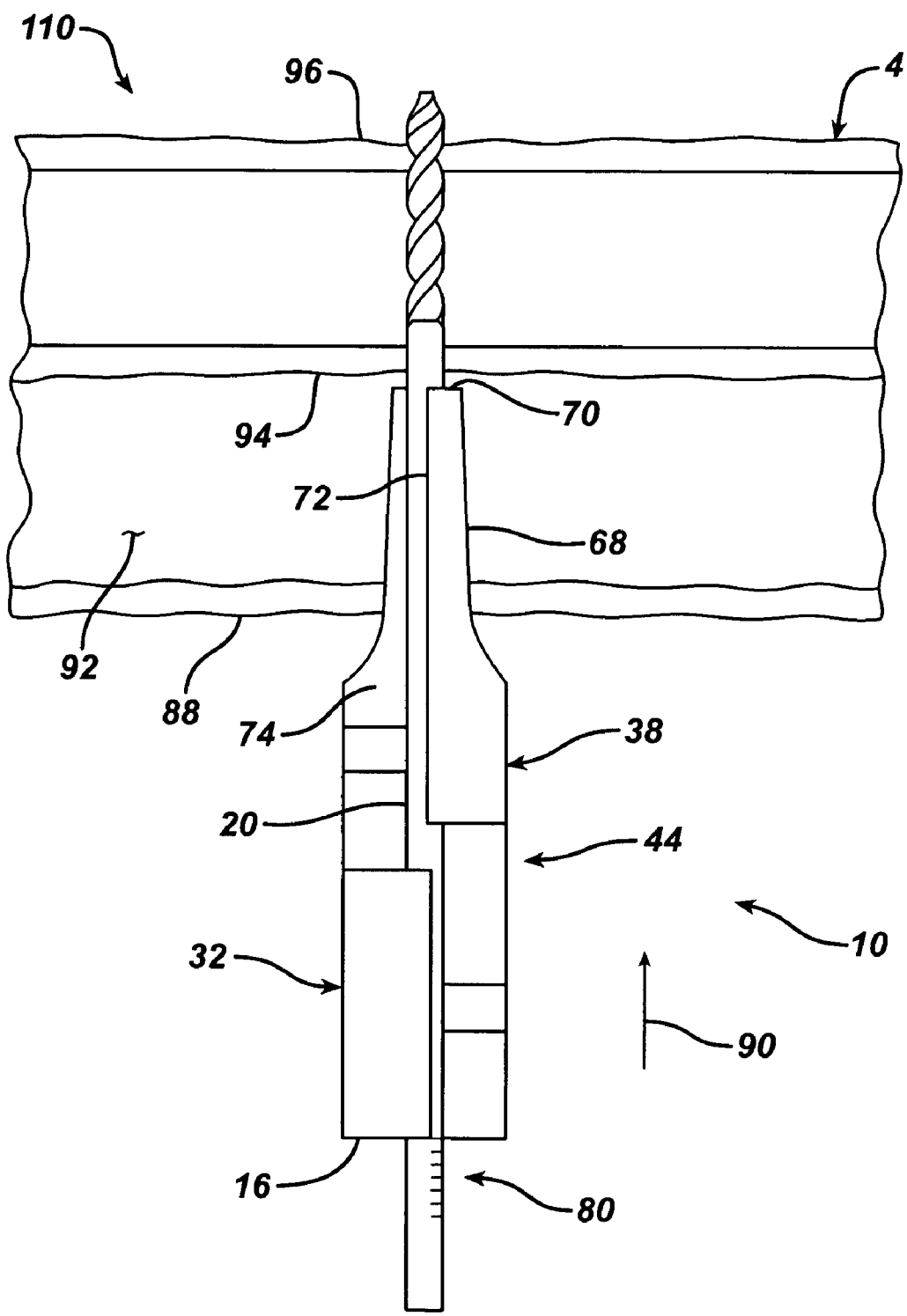
FIG. 19 is a partial plan view of kit of FIG. 16 with the drill of FIG. 14 in position in the sleeve assembly of FIG. 1, both being inserted into a patient.

Referring now to FIG. 19, the trocar portions 68 are shown for use in percutaneous insertion of the depth gage 10. The tip or end 70 of the trocar portion 68 is inserted in an incision in skin 8 of the patient. The depth gage 10 is inserted in the direction of arrow 90 until the end 70 of the trocar portion passes through soft tissue 92 and the tip or end 70 rests against medial or lateral cortical surface 94 of the long bone 4. The drill 12 is then advanced until the drill 12 passes through the lateral cortical surface 96 of the long bone 4. The indicia 80 on the drill 12 are then used to determine the proper cortical screw for insertion through the hole.

Figure 21:
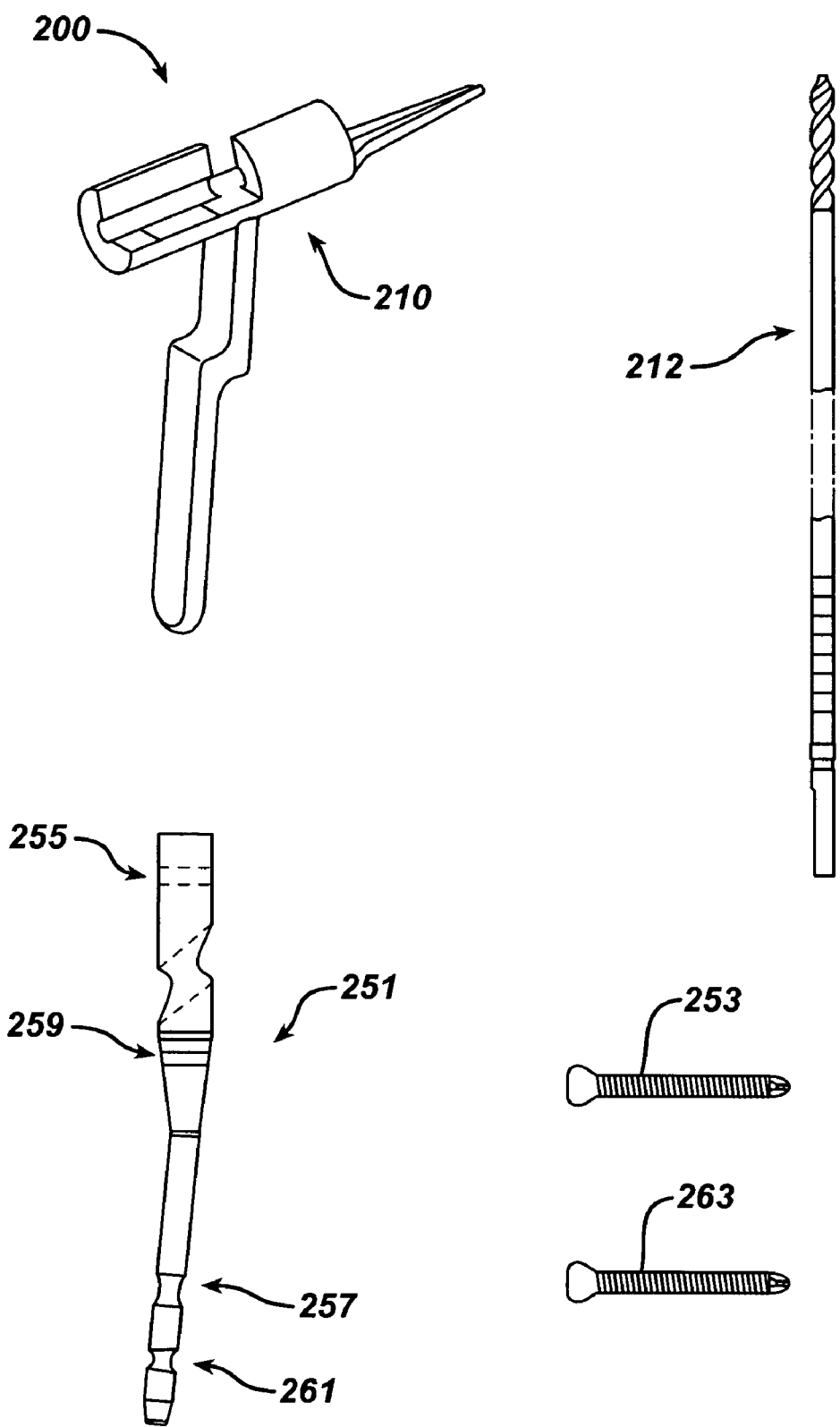
FIG. 21 is a plan view of another kit for performing trauma surgery in accordance to another embodiment of the present invention.

Referring now to FIG. 21, another embodiment of the present invention is shown as kit 210 for use with orthopaedic surgery. The kit 210 includes an intramedullary nail 251, a screw, 253, a drill 212, and a depth gage 210. The intramedullary nail 251 can be any nail capable of insertion in the medullary canal of a long bone. The intramedullary nail 251 may as shown in FIG. 21, include a first proximal transverse opening 255. The intramedullary nail 251 may further include a first distal transverse opening 257. It should be appreciated that the intramedullary nail 251 may include additional transverse holes, for example, a second proximal transverse opening 259 and a second distal transverse opening 261.

The depth gage 210 of the kit 200 may be similar to the gage 10 of FIGS. 1-10. The drill 212 may be similar to the drill 12 of FIGS. 14 and 15. The screw 253 may be any commercially available screw. The screw 253 may be adapted to, for example, fit into first proximal transverse opening 255 of the intramedullary nail 251. It should be appreciated that the proximal cortical screw 253 may be fittable into both first proximal transverse opening 255 and the second proximal transverse opening 259.

The kit 210 may further include additional screws, for example, distal cortical screws 263. One of the distal cortical screw 263 may be fitted, for example, into first distal transverse opening 257. One of the distal cortical screws 263 may likewise be fittable into the second distal transverse opening 261.

Figures 22, 22A:
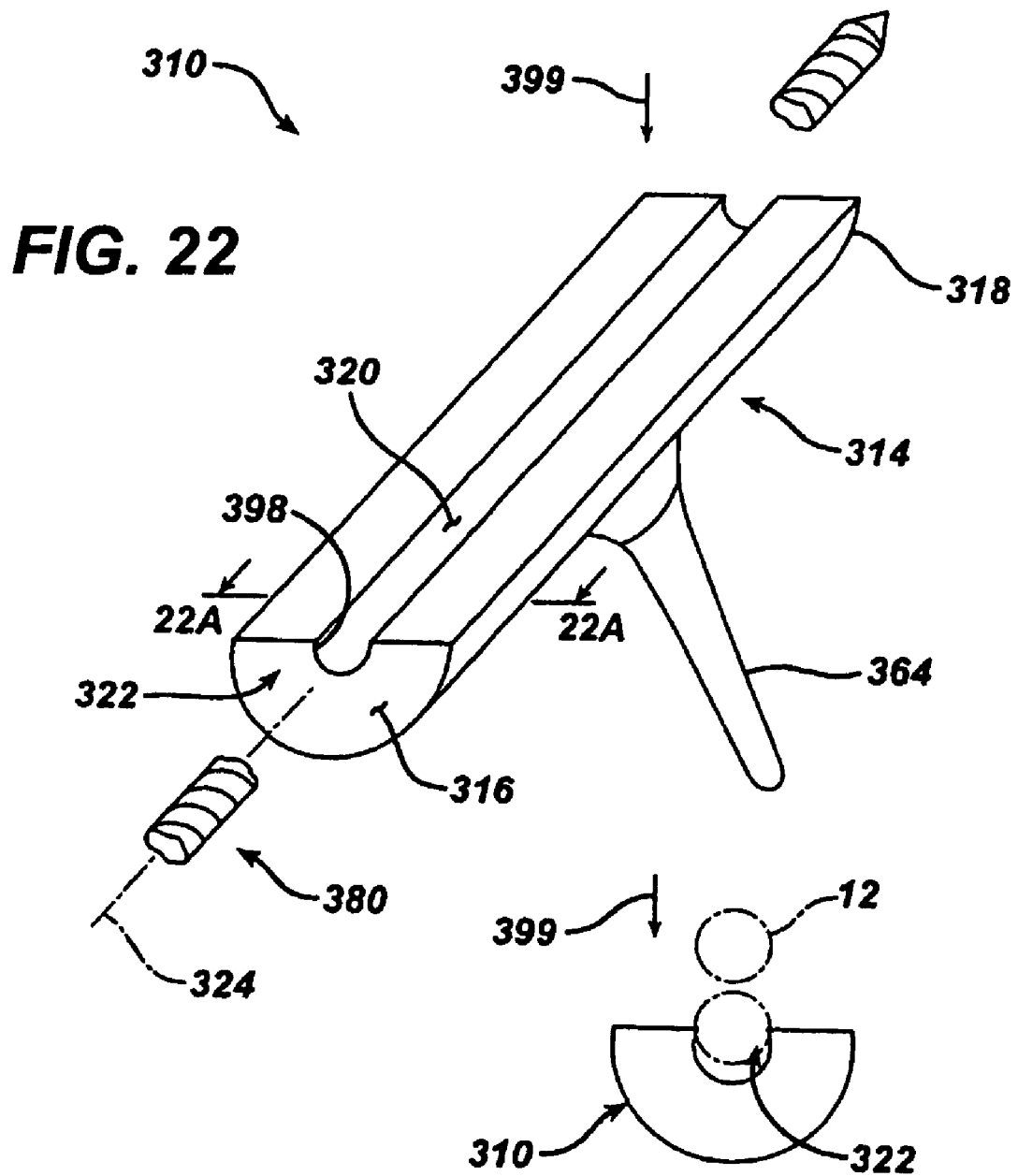
FIG. 22 is a perspective view of a sleeve assembly in accordance to another embodiment of the present invention with a lip formed onto the sleeve.
FIG. 22A is a cross sectional view of FIG. 22 along the line 22A-22A in the direction of the arrows.

Referring now to FIG. 22, yet another embodiment of the present invention is shown as depth gage 310. Depth gage 310 includes a body 314 having a generally hemi-cylindrical shape. The body 314 includes a longitudinal opening 322 having a longitudinal axis 324. The opening 322 is adapted for receiving the drill 12. The body 314 includes a first end 316 and an opposed end 318. The opening 322 defines an inner periphery 320 of the body 314. The inner periphery 320 includes a detent 398 which the drill 12 must engage as the depth gauge 310 is snapped to be inserted when installed in the direction of arrow 399. The depth gage 310 further includes a handle 364 for use in installing the depth gage 310 unto the drill 12. The drill 12 includes indicia 80 which together with the first end 316 of the body 314 of the depth gage 310 are used to determine the proper size of a screw to be used in the patient.

Referring now to FIG. 22A, the drill 12 is shown being installed into the depth gage 310 in the direction of arrow 399. As can be seen detent 398 is deflected into a position shown in phantom as the drill 12 passes into the opening 322 of the depth gage 310.

Figure 23:
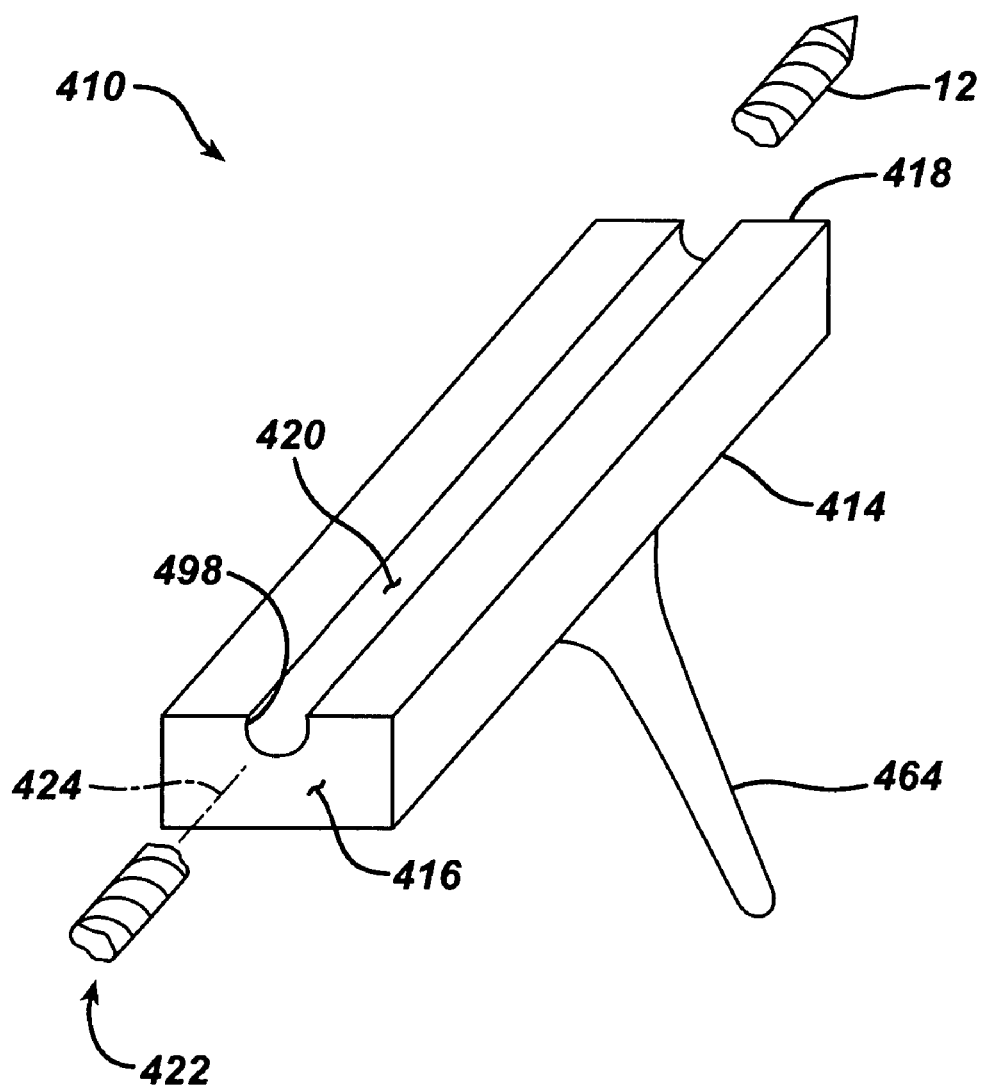
FIG. 23 is a perspective view of a sleeve assembly in accordance to yet another embodiment of the present invention with an opening that contains the drill.

Referring now to FIG. 23, yet another embodiment of the present invention is shown as depth gage 410. The depth gage 410 includes a body 414 which has a generally rectangular shape. The body 414 includes a first end 416 and a spaced apart second end 418. The body 414 includes an inner periphery that defines a longitudinal opening 422 about opening centerline 424. The opening 422 slidably receives the drill 12. The indicia 80 that are located on the drill 12 together with the first end 416 of gage 410 are used to determine the proper screw to be used in surgery. As shown in FIG. 23, the depth gage 410 includes a handle 464 connected to the body 414. The depth gage 410 includes a protrusion or detent 498 similar to the protrusion 398 of the gage 310 of FIG. 22.

Figure 24:
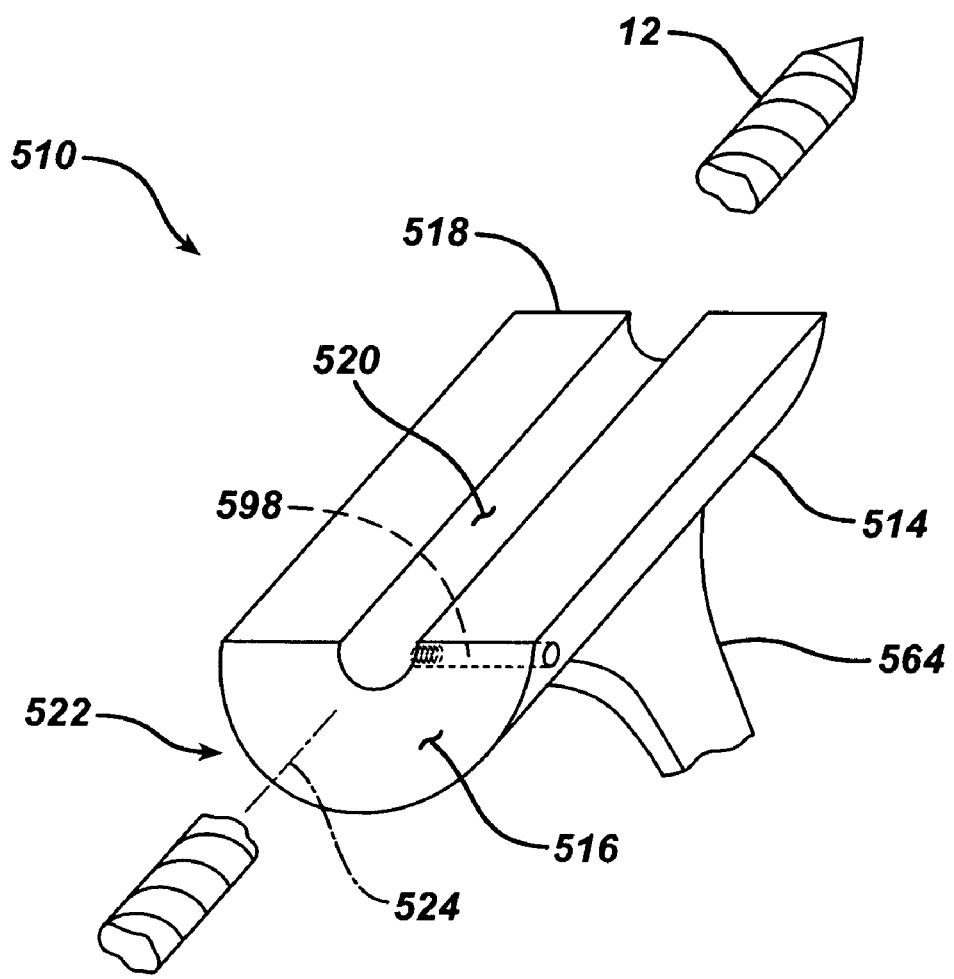
FIG. 24 is a perspective view of a sleeve assembly in accordance to another embodiment of the present invention with an spring detent that contains the drill.

Referring now to FIG. 24, yet another embodiment of the present invention is shown as depth gage 510. The depth gage 510 includes a body 514 having a generally hemi-cylindrical shape. The body 514 defines a hemi-cylindrical inner periphery 520, which defines a longitudinal opening 522 about longitudinal centerline 524. The body 514 includes a first end 516 and a second end 518.

The drill 12 includes indicia 80 thereon that together with the first end 516 of gage 510 are used to determine the particular screw for use in the surgery. The depth gage 510 further includes a detent 598 that is positioned into the longitudinal opening 522 and that is used to restrain the drill 12 within the longitudinal opening 522. The depth gage 510 may, as is shown in FIG. 24, include a handle 564 connected to the body 514.

Figure 25:
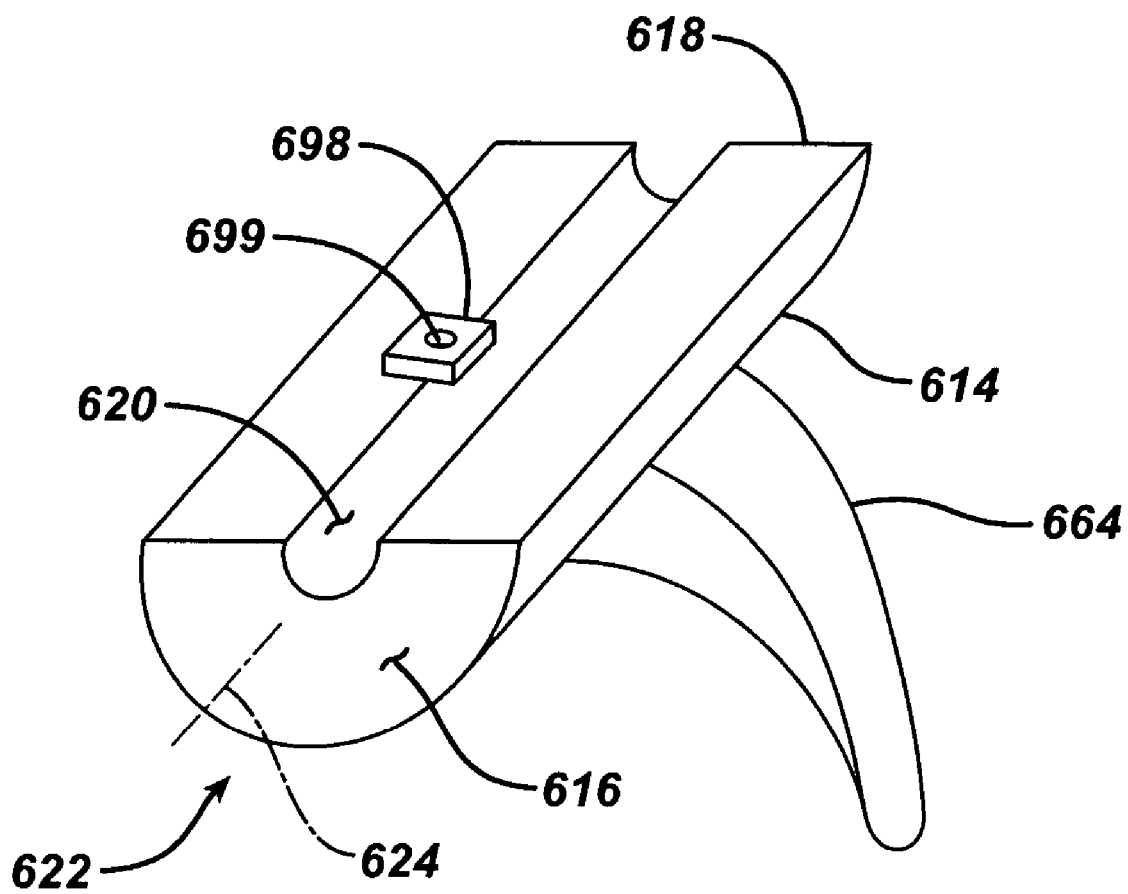
FIG. 25 is a perspective view of a sleeve assembly in accordance to yet another embodiment of the present invention with a lip component secured to the sleeve.

Referring now to FIG. 25, another embodiment of the present invention is shown as depth gage 610. The depth gage 610 includes a generally hemi-cylindrical body 614 having a first end 616 and an opposed second end 618. The body 614 defines an inner periphery 620 which defines a longitudinal opening 622 about longitudinal centerline 624. The depth gage 610 further includes a tab 698 which extends into the longitudinal opening 622 and is used to restrain the drill within the longitudinal opening 622. The tab 698 may be secured to the body 614 with any suitable manner. For example and as shown in FIG. 25, the tab 698 is secured to the body 614 by means of screw 699. The depth gage 610 may further include a handle 664 secured to the body 614 of the depth gage 610.

Figure 26:
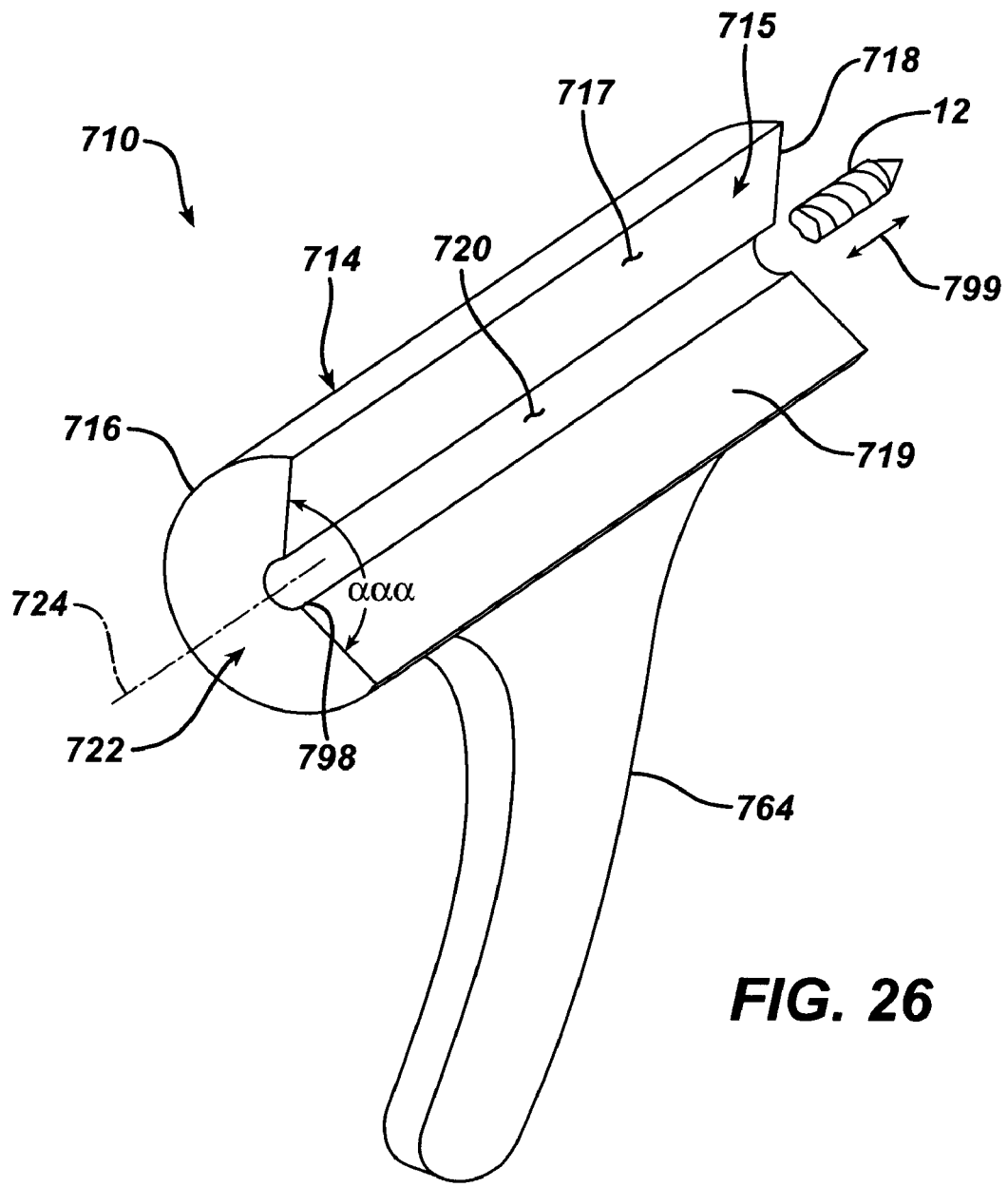
FIG. 26 is a perspective view of a sleeve assembly in accordance to yet another embodiment of the present invention with an opening that contains the drill and has side walls to guide the drill during installation.

Referring now to FIG. 26, yet another embodiment is shown is depth gage 710. The depth gage 710 includes a body 714 having a first end 716 and an opposed second end 718. The body 714 has a generally cylindrical shape and has a sector 715 of the cylindrical body 714 removed. The drill 12 is inserted into the gage 710 in the direction of arrow 799 through the sector 715. The body 714 defines an inner periphery 720 which defines a longitudinal opening 722 about longitudinal centerline 724 of the body 710. Sector 715 defined faces 717 and 719 which define an acute angle $\alpha\alpha\alpha$ therebetween.

The angle $\alpha\alpha\alpha$ is selected to be an acute angle having, for example, an angle from about 10° to 60°. The angle $\alpha\alpha\alpha$ establishes a detent 798 about the inner periphery 720 of the body 714 of the depth gage 710 so that the drill 12 may be snapped in place when inserted in the direction arrow 799. The depth gage 710 may further include a handle 764 secured to the body 714 of the depth gage 710.

Figure 27:
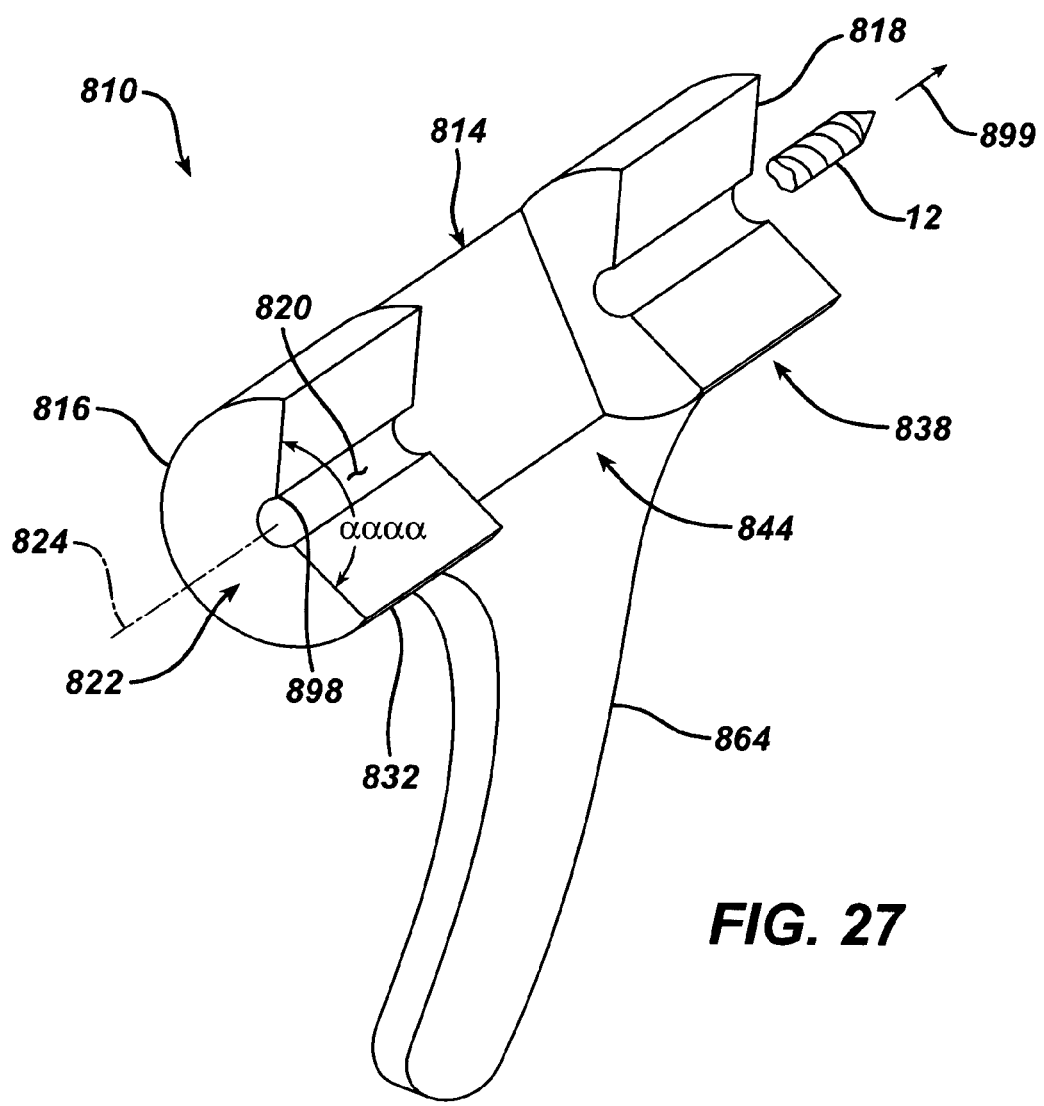
FIG. 27 is a perspective view of a sleeve assembly in accordance to yet another embodiment of the present invention with an opening that contains the drill and has side walls to guide the drill during installation and relief In the middle of the body.

Referring now to FIG. 27, yet another embodiment of the present invention is shown as depth gage 810. The depth gage 810 includes a body 814 having a first end 816 and an opposed second end 818. The body 814 has a shape somewhat similar to the shape of the body 714 of the depth gage 710 of FIG. 26 but further includes a three-portion configuration including a first portion 832 extending from the first end 816 of the body 814. The first portion 832 has a shape generally similar to that of the body 714 of the gage 710 of FIG. 26. The body 814 further includes a second portion 838 extending from the second end 818 of the body 814. The second portion 838 is similar to the shape of the body 714 of the depth gage 710. The body 814 further includes a middle portion 844 positioned between the first portion 832 and the second portion 838.

The body 814 includes an inner periphery 820, which defines a longitudinal opening 822 which defines a longitudinal centerline 824. The inner periphery 820 of the longitudinal opening 822 extends at an angle $\alpha\alpha\alpha\alpha$ which is less than 180°. The angle $\alpha\alpha\alpha\alpha$ creates a wrap around the drill by the periphery 820 of the opening 822 such as to provide a detent 898 to cause the drill 12 to snap in place when inserted in the direction of arrow 899. The depth gage 810 may further include a handle 864 extending from the body 814 of the depth gage 810.

Figures 28, 29:
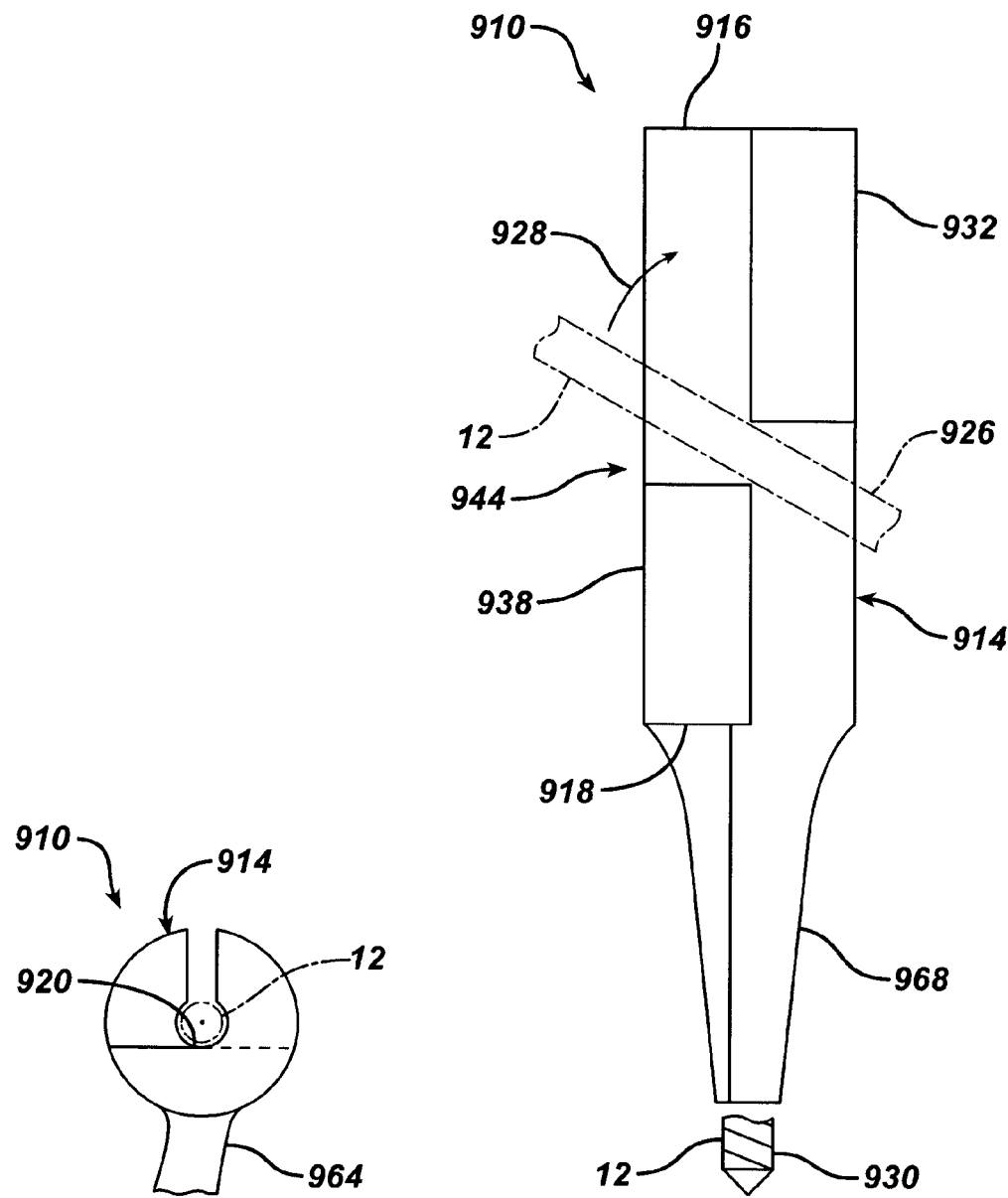
FIG. 28 is a plan view of a sleeve assembly in accordance to yet another embodiment of the present invention without a snap-in feature.
FIG. 29 is an end view of the sleeve assembly of FIG. 28.

Referring now to FIG. 28, yet another embodiment of the present invention is shown as drill gage 910. The drill gage 910 is somewhat similar to the drill gage 10 of FIGS. 1-10 except that the drill gage 910 does not provide for a snap in feature. The drill gage 910 includes a body 914 defining a first portion 932 somewhat similar to the first portion 32 of the gage 10 of FIGS. 1-10. The first portion 932 does not include a snap-in feature. The first portion 932 of the gage 910 extends from first end 916 of the body 914 of the gage 910.

The gage 910 further includes a second portion 938 similar to the second portion 38 of the gage 10 of FIGS. 1-10 except the second portion 938 of the gage 910 does not include a snap in feature. The second portion 938 extends from second end 918 of the body 914 of the gage 910. The gage 910 further includes a trocar 968 extending from the second end 918 of the body 910.

The gage 910 is fitted over drill 12 by placing the drill 12 in first position 926 and rotating the drill in the direction of 928 until the drill is in the second position 930 as shown in phantom.

Referring now to FIG. 29, the body 914 of the gage 910 defines an inner arcuate periphery 920 for slidably fitting with the drill 12. The gage 910 may include a handle 964 extending from the body 914 of the gage 910.

Figure 30:
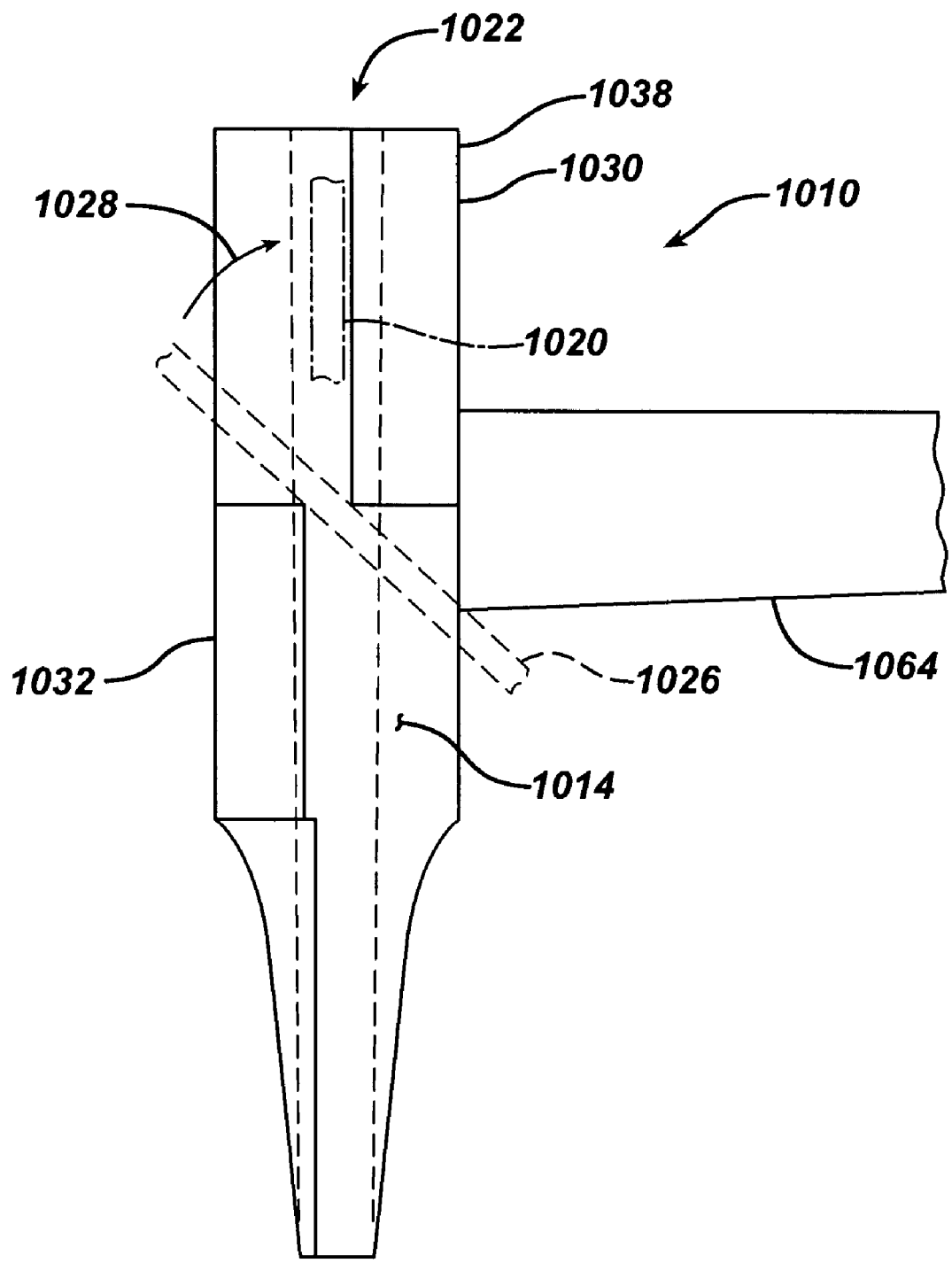
FIG. 30 is a plan view of a sleeve assembly in accordance to yet another embodiment of the present invention without a middle relief portion.

Referring now to FIG. 30, yet another embodiment of the present invention is shown as depth gage 1010. Depth gage 1010 is similar to the gage 10 of FIGS. 1-10 except that the depth gage 1010 includes a body 1014 that has a first portion 1032 and a second portion 1038 similar to the first portion 32 and the second portion 38, respectively, of the gage 10 FIGS. 1-10. However the depth gage 1010 does not include a middle portion such as middle portion 44 of the gage 10 of FIGS. 1-10.

The depth gage 1010 includes an inner periphery, which defines a transverse opening 1022 for receiving the drill 12. The drill 12 is installed by first placing the drill 12 in first position 1026 shown in hidden lines and rotating the drill 12 in first position 1026 in the direction of arrow 1028 toward second position 1020 shown in phantom. The depth gage 1010 may further include a handle 1064 extending from the body 1014 of the depth gage 1010.

Figure 31:
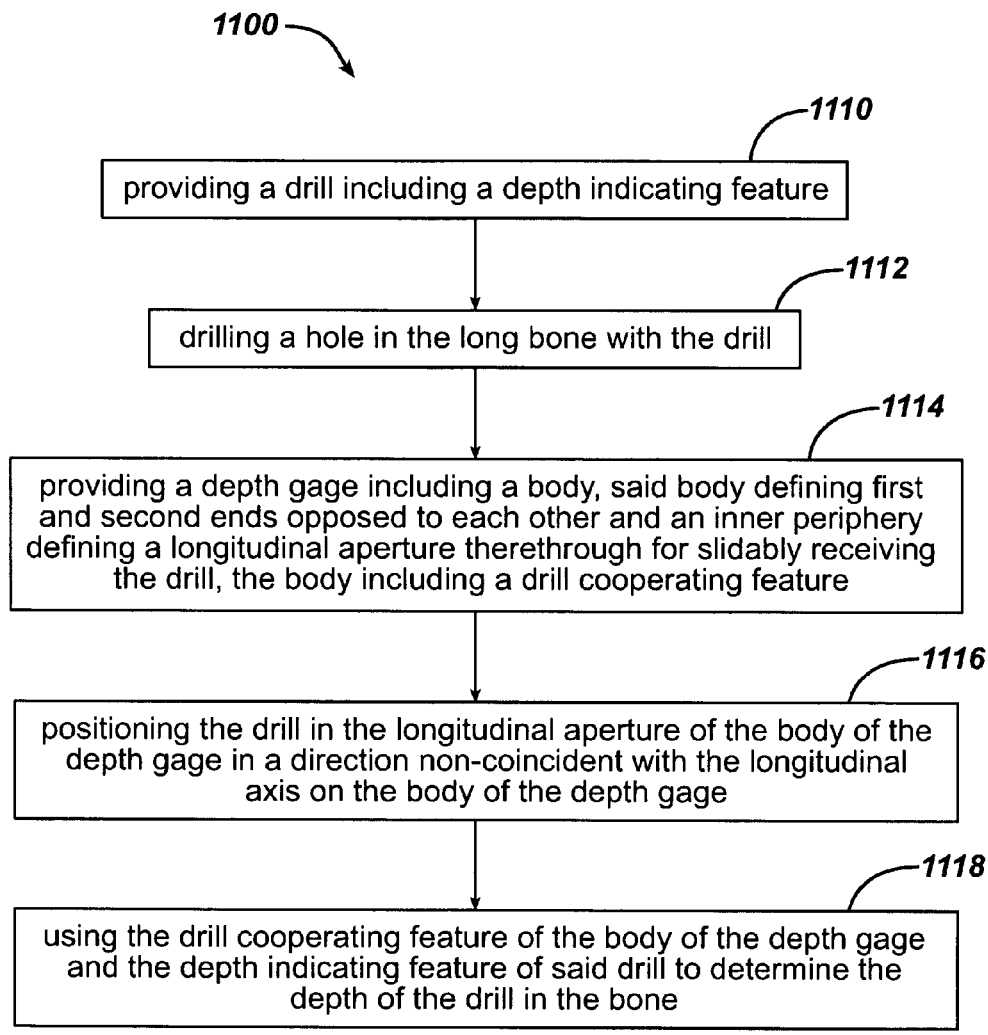
FIG. 31 is a flow chart of a method for performing trauma surgery in accordance with an yet another embodiment of the present invention.

Referring now to FIG. 31, yet another embodiment of the present invention is shown as a method for performing orthopedic surgery 1100. The method 1100 for performing orthopedic surgery upon a long bone include the first step 1110 of providing a drill including a depth indicating feature. The method 1100 further includes a second step 1112 of drilling a hole in the long bone with a drill. The method 1100 further includes a third step 1114 of providing a depth gage including a body. The body defines first and second ends opposed to each other and an inner periphery defining a longitudinal aperture through the body. The longitudinal aperture is utilized for slidably receiving the drill. The body includes a drill cooperating feature. The method 1100 further includes a fourth step 1116 of positioning the drill in the longitudinal aperture of body of the depth gage in a direction non-coincident with the longitudinal axis on the body of the depth gage. The method 1100 further includes a fifth step 1118 of using the drill cooperating feature of the body of the depth gage and the depth indicating feature of the drill to determine the depth of the drill in the bone.

Figure 32:
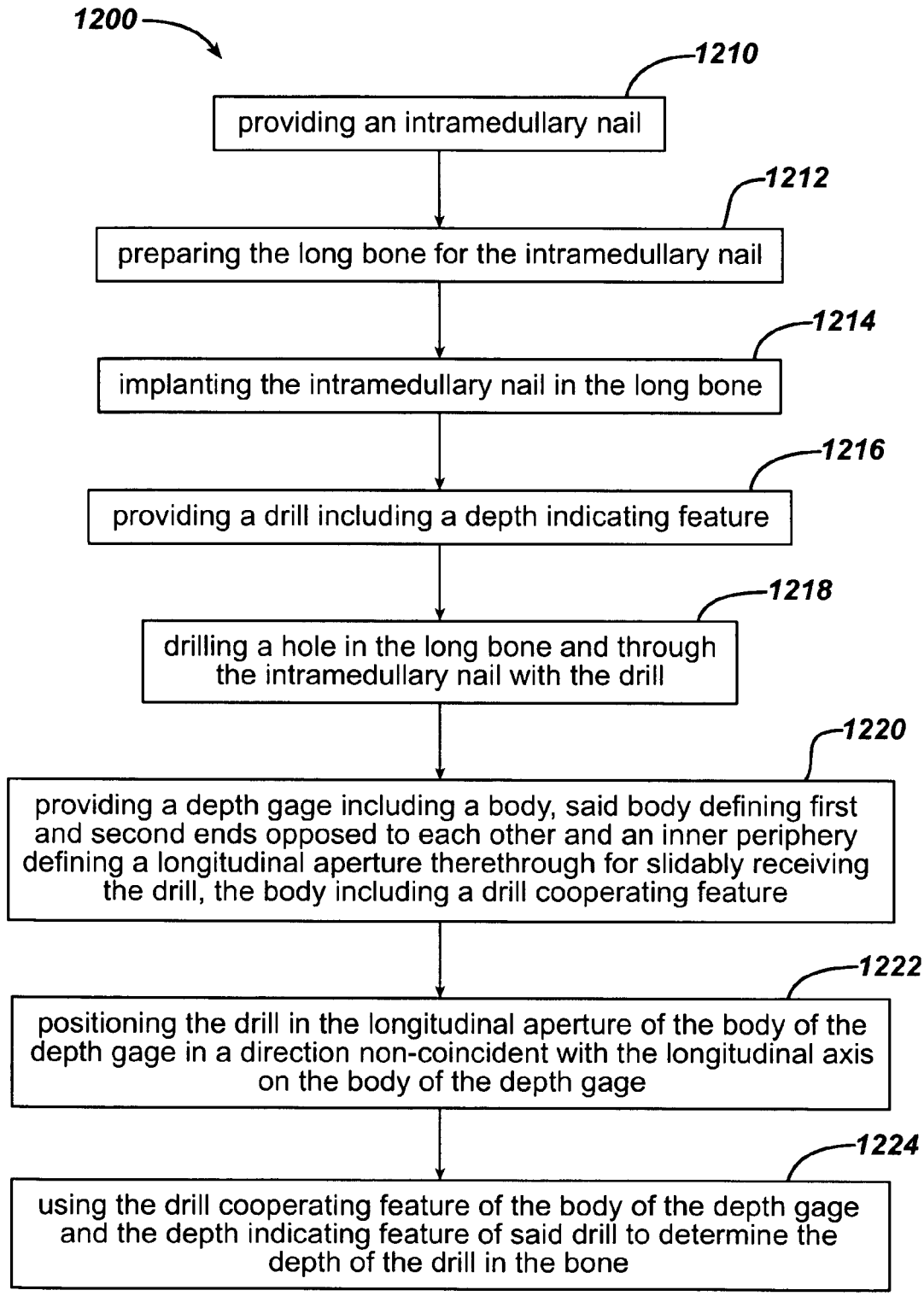
FIG. 32 is a flow chart of another method for performing trauma surgery in accordance with another embodiment of the present invention accordance with another embodiment of the present invention.

According to the present invention and referring now to FIG. 32, yet another embodiment of the present invention is shown as method 1200 of implanting an intramedullary nail in a long bone. The method 1200 includes a first step 1210 for providing an intramedullary nail. The method 1200 further includes a second step 1212 of preparing the long bone for the intramedullary nail. The method 1200 further includes a third 1214 of implanting the intramedullary nail in the long bone. The method 1200 further includes a fourth step 1216 of providing a drill including a depth indicating feature. The method 1200 further includes a fifth step 1218 of drilling a hole in the long bone and through the intramedullary nail of the drill.

The method 1200 further includes a sixth step 1220 of providing a depth gage including a body. The body defines first and second ends of the body opposed to each other and an inner periphery defining a longitudinal aperture through the body. The longitudinal aperture is utilized for slidably receiving the drill. The body includes a drill cooperating feature. The method 1200 further includes a seventh step 1222 of positioning the drill in the longitudinal aperture of the body of the depth gage in the direction non-coincident with the longitudinal axis of the body of the depth gage. The method 1200 further includes an eighth step 1224 of using the drill cooperating feature of the body of the depth gage and the depth indicating feature of the drill to determine the depth of the drill in the bone.

Although the present invention and its advantages have been described in detail, it should be understood that various changes, substitutions, and alterations can be made therein without departing from the spirit and scope of the present invention as defined by the appended claims.

We claim:

1. A depth gage for use with a drill in orthopaedics comprising a body, said body defining first and second ends opposed to each other and an inner periphery defining a longitudinal aperture therethrough for slidably receiving the drill, the longitudinal aperture defining a longitudinal axis thereof, said body comprising,
   a first end portion comprising an arcuate cross-sectional periphery about the longitudinal axis defining a first lateral opening to the longitudinal aperture, the first end portion comprising a radially extending face facing in a first lateral direction;
   a second end portion longitudinally staggered relative the first end portion, the second end portion comprising an arcuate cross-sectional periphery about the longitudinal axis defining a second lateral opening to the longitudinal aperture, the second end portion comprising a radially extending face facing in a second lateral direction, the first and second lateral directions being opposite one another
said body being adapted to permit the drill to be installed in the longitudinal aperture in a first position having a direction non-coincident with the longitudinal axis and wherein the drill can be shifted to a second position substantially aligned with the longitudinal axis and the drill can be rotated and advanced longitudinally in the aperture.

2. The depth gage as in claim 1 wherein at least a portion of the first arcuate periphery extends an angle from about 185 degrees to about 195 degrees about the longitudinal axis of the longitudinal aperture.

3. The depth gage as in claim 1 wherein said body is adapted to permit the drill to be positioned into the longitudinal opening in a first direction perpendicular to the longitudinal axis of the longitudinal opening and then to permit the drill to be rotated into position in the longitudinal aperture.

4. The depth gage as in claim 1, further comprising a middle portion of said body having portion of the cross section thereof along a plane perpendicular to the, longitudinal axis of the aperture defining a periphery for tangential contact with the drill.

5. The depth gage as in claim 1, wherein the arcuate periphery of at least one said first end portion and said second end portion extends an angle greater than about 185 degrees about the longitudinal axis of the longitudinal aperture.

6. The depth gage as in claim 1, wherein the first and second faces are generally co-planar.

7. The depth gage as in claim 1, wherein the first and second end portions are longitudinally spaced from one another.

* * * * *

UNITED STATES PATENT AND TRADEMARK OFFICE
CERTIFICATE OF CORRECTION

| | |
|---|---|
| PATENT NO. | : 7,753,914 B2 |
| APPLICATION NO. | : 11/238456 |
| DATED | : July 13, 2010 |
| INVENTOR(S) | : Marc E. Ruhling et al. |

It is certified that error appears in the above-identified patent and that said Letters Patent is hereby corrected as shown below:

Column 1,
Line 25, before "often" delete "-"

Column 4,
Line 14, after "a" delete "The"

Column 6,
Lines 33, replace "In" with --in--

Column 6,
Line 43, after "with" delete "an"

Column 6,
Lines 47-48, delete second occurrence of "accordance with another embodiment of the present invention"

Column 7,
Line 5, after "For example and" delete "is"

Column 7,
Line 9, replace "For example and is" with --For example and as--

Column 7,
Line 16, replace "For example and is" with --For example and as--

Column 7,
Line 39, replace "180" with --180°--

Signed and Sealed this
Fifth Day of March, 2013

Teresa Stanek Rea
*Acting Director of the United States Patent and Trademark Office*

Column 7,
Line 41, replace "is" with --as--

Column 7,
Line 46, replace "is" with --as--

Column 7,
Line 54, replace "is" with --as--

Column 8,
Line 20, replace "i-s" with --is--

Column 8,
Line 52, replace "is" with --as--

Column 8,
Line 58, after "66" insert --that--

Column 9,
Line 42, replace "depth gage 110" with --depth gage 10--

Column 10,
Line 15, replace "is" with --as--

Column 11,
Line 56, replace "shown is" with --shown as--

Column 12,
Line 60, after "gage 10" insert --of--

Column 13,
Line 31, after "includes a third" insert --step--

Column 14,
Line 41, after "to the" delete ","